(12) United States Patent
Ashkar et al.

(10) Patent No.: US 11,053,290 B2
(45) Date of Patent: Jul. 6, 2021

(54) MODIFIED TAMM-HORSFALL PROTEIN AND RELATED COMPOSITIONS AND METHODS OF USE

(71) Applicant: Indiana University Research and Technology Corporation, Indianapolis, IN (US)

(72) Inventors: Tarek Maurice Ashkar, Zionsville, IN (US); Radmila Micanovic, Indianapolis, IN (US)

(73) Assignees: Indiana University Research and Technology Corporation, Indianapolis, IN (US); The United States Government as Represented by the Department of Veterans Affair, Washington D.C., DC (US)

( * ) Notice: Subject to any disclaimer, the term of this patent is extended or adjusted under 35 U.S.C. 154(b) by 0 days.

(21) Appl. No.: 15/771,036

(22) PCT Filed: Oct. 28, 2016

(86) PCT No.: PCT/US2016/059379
§ 371 (c)(1),
(2) Date: Apr. 25, 2018

(87) PCT Pub. No.: WO2017/075393
PCT Pub. Date: May 4, 2017

(65) Prior Publication Data
US 2018/0305420 A1    Oct. 25, 2018

Related U.S. Application Data

(60) Provisional application No. 62/401,759, filed on Sep. 29, 2016, provisional application No. 62/248,809, filed on Oct. 30, 2015.

(51) Int. Cl.
| | |
|---|---|
| *A61K 38/00* | (2006.01) |
| *C07K 14/47* | (2006.01) |
| *C07K 14/435* | (2006.01) |
| *A61P 13/12* | (2006.01) |
| *A61K 35/00* | (2006.01) |
| *A61K 35/22* | (2015.01) |
| *A61K 38/17* | (2006.01) |

(52) U.S. Cl.
CPC .............. *C07K 14/47* (2013.01); *A61P 13/12* (2018.01); *C07K 14/435* (2013.01); *A61K 35/00* (2013.01); *A61K 35/22* (2013.01); *A61K 38/00* (2013.01); *A61K 38/1709* (2013.01)

(58) Field of Classification Search
None
See application file for complete search history.

(56) References Cited

U.S. PATENT DOCUMENTS

| | | | |
|---|---|---|---|
| 2009/0317808 A1* | 12/2009 | Sameah-Greenwald | ................... C12Q 1/6883 435/6.11 |
| 2015/0005240 A1* | 1/2015 | Castellano | ............. A61K 38/16 514/20.9 |

OTHER PUBLICATIONS

Pennica, Science, New Series, vol. 236, No. 4797 (Apr. 3, 1987), pp. 83-88 (Year: 1987).*
Pennica, Science, 1987, 236, 83-88 (Year: 1987).*
Xie, Antimicrobial Agents and Chemotherapy, Jan. 2010, p. 191-196 (Year: 2010).*
International Search Report and Written Opinion issued by the ISA/US, Commissioner for Patents, dated Mar. 8, 2017, for International Application No. PCT/US2016/059379; 11 pages.

\* cited by examiner

*Primary Examiner* — Satyanarayana R Gudibande
(74) *Attorney, Agent, or Firm* — Faegre Drinker Biddle & Reath LLP

(57) ABSTRACT

Embodiments of the present disclosure provide polypeptides, related materials and compositions, and methods for their use. In certain embodiments, the present disclosure provides a monomeric Tamm-Horsfall Protein polypeptide, or a biologically active truncation thereof. Other embodiments provide polynucleotides encoding a polypeptide described herein, nucleic acid expression vectors including the polynucleotides, and recombinant host cells including the expression vector. Yet other embodiments provide pharmaceutical compositions including a polypeptide described herein. Also provided are methods for treating a renal disease, disorder, or condition in a subject and/or modulating an immune response in a subject.

19 Claims, 18 Drawing Sheets
Specification includes a Sequence Listing.

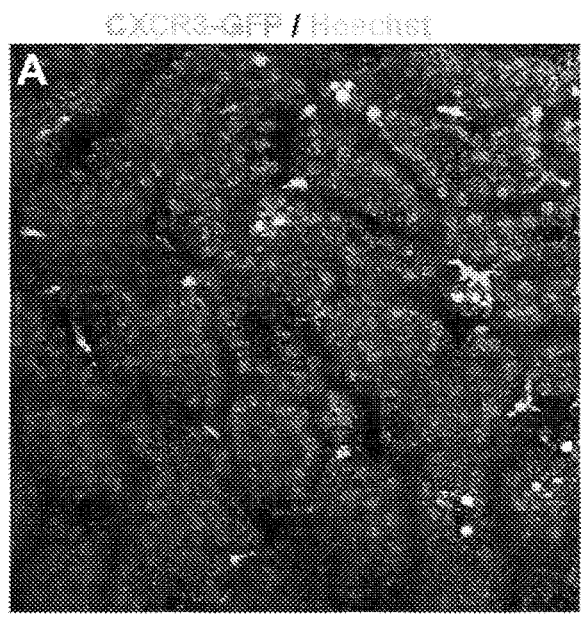 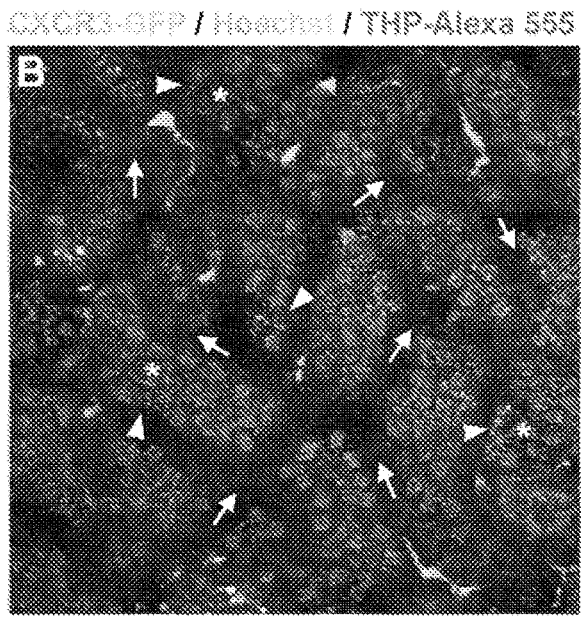
FIG. 17A  FIG. 17B
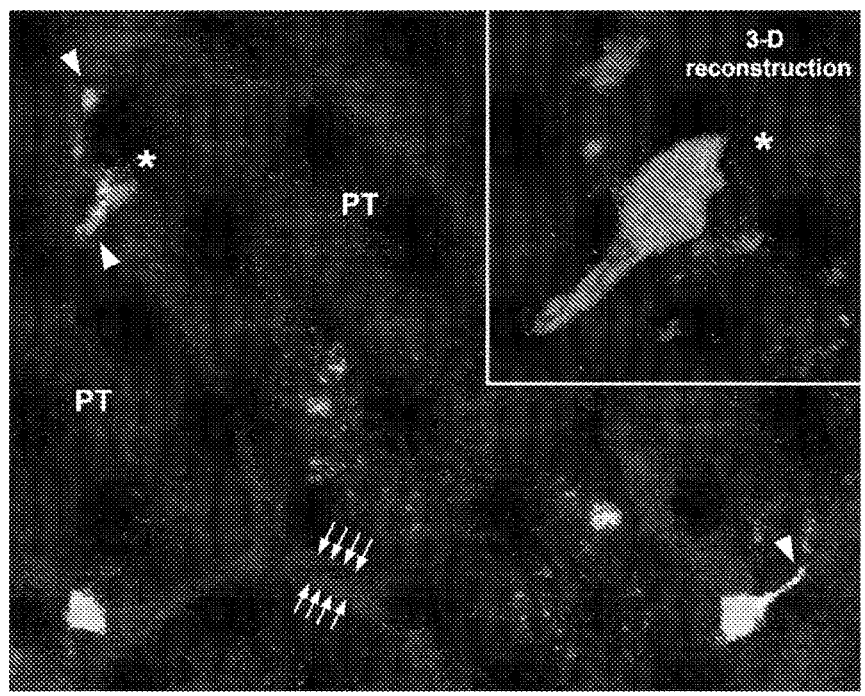
FIG. 18

MODIFIED TAMM-HORSFALL PROTEIN AND RELATED COMPOSITIONS AND METHODS OF USE

CROSS-REFERENCE TO RELATED APPLICATIONS

This application is a U.S. National Stage Application under 35 U.S.C. § 371 of International Patent Application No. PCT/US2016/059379, filed Oct. 28, 2016, which claims the benefit of U.S. Provisional Patent Application Nos. 62/248,809, filed on Oct. 30, 2015, and 62/401,759, filed on Sep. 29, 2016, each of which is incorporated herein by reference in its entirety.

STATEMENT REGARDING FEDERALLY SPONSORED RESEARCH

This invention was made with government support under TR000006 awarded by the National Institutes of Health and 101-BX001071 merit award through the Veterans Administration. The government has certain rights in the invention.

SEQUENCE LISTING

The instant application contains a Sequence Listing which has been submitted via EFS-web in computer readable form, and is hereby incorporated by reference in its entirety. The ASCII copy, created on Sep. 29, 2016, is named IURTC_2016_026_02_SEQ_LIST_ST25.txt, and is 25,678 bytes in size.

FIELD

The present disclosure generally relates to polypeptides, polynucleotides encoding the polypeptides, pharmaceutical compositions including the polypeptides or polynucleotides, the use of such polynucleotides and compositions, and more specifically, the use of the polynucleotides and compositions in the treatment of a renal disease, disorder, or condition.

BACKGROUND

Tamm-Horsfall protein (THP) was discovered by Igor Tamm and Frank Horsfall in 1950 when they precipitated a protein from human urine that inhibited hemagglutination of viruses. The protein is expressed exclusively by renal tubular cells lining the thick ascending limb (TAL) of the loop of Henle. In 1985, Muchmore and Decker isolated a protein named uromodulin from the urine of pregnant women that had immunosuppressive effects on T cell in vitro. Uromodulin was demonstrated to be identical to Tamm-Horsfall protein through amino acid sequencing in 1987.

The synthesized protein is cotranslationally translocated into the endoplasmic reticulum, glycosylated, glypiated, secreted, and anchored to the apical tubular cell membrane. From this site the protein is released by protease cleavage and excreted in the urine, where it is the most abundant urinary protein in healthy individuals. In the urine, the protein aggregates and can precipitate, and is the main constituent of hyaline urinary casts.

Recent discoveries have underscored the importance of THP (encoded by the UMOD gene) as a regulatory protein in health and in various conditions, such as medullary cystic kidney disease, glomerulocystic kidney disease, urinary tract infections, nephrolithiasis, and acute kidney injury

SUMMARY

In one aspect, the present disclosure provide purified or isolated polypeptides including an amino acid sequence at least 85% identical to an amino acid sequence chosen from SEQ ID NO: 2 (hUMOD-ΔZP), SEQ ID NO: 3 (hUMOD-EGF+D8C), SEQ ID NO: 4 (hUMOD-EGF), SEQ ID NO: 5, SEQ ID NO: 6 and SEQ ID NO: 7. In some embodiments the polypeptides include an amino acid sequence at least 95% identical to an amino acid sequence chosen from SEQ ID NO: 2 (hUMOD-ΔZP), SEQ ID NO: 3 (hUMOD-EGF+D8C), SEQ ID NO: 4 (hUMOD-EGF), SEQ ID NO: 5, SEQ ID NO: 6 and SEQ ID NO: 7. In other embodiments, the polypeptides have an amino acid sequence chosen from SEQ ID NO: 2 (hUMOD-ΔZP), SEQ ID NO: 3 (hUMOD-EGF+D8C), SEQ ID NO: 4 (hUMOD-EGF), SEQ ID NO: 5, SEQ ID NO: 6 and SEQ ID NO: 7.

In another aspect, the present disclosure provides a polynucleotide encoding a polypeptide of any aspect or embodiment described herein. In another aspect, the present disclosure provides nucleic acid expression vectors including the polynucleotide. In some embodiments, the polynucleotide is operably linked to a promoter sequence. In some embodiments, the polynucleotide is operably linked to a signal sequence. In certain embodiments, the polynucleotide is operably linked to both a promoter sequence and a signal sequence. In another aspect, the present disclosure provides a host cell that includes a nucleic acid expression vector of any aspect or embodiment described herein.

Another aspect provides a pharmaceutical composition including a polypeptide of any aspect or embodiment described herein, and a pharmaceutically acceptable carrier. In some embodiments, the pharmaceutical composition includes a purified or isolated polypeptide including an amino acid sequence at least 85% identical to an amino acid sequence according to SEQ ID NO: 1 (hUMOD; Accession: P07911.1), either in combination with one or more polypeptides described herein, or on its own. In some such embodiments, the pharmaceutical composition also includes one or more other polypeptides described herein.

Further aspects described herein provide a method for treating at least one renal disease, disorder, or condition in a subject, the method including administering to the subject an effective amount of a purified or isolated polypeptide including an amino acid sequence at least 85% identical to an amino acid sequence chosen from SEQ ID NO: 2 (hUMOD-ΔZP), SEQ ID NO: 3 (hUMOD-EGF+D8C), SEQ ID NO: 4 (hUMOD-EGF), SEQ ID NO: 5, SEQ ID NO: 6, and SEQ ID NO 7; a purified or isolated polypeptide comprising an amino acid sequence at least 85% identical to an amino acid sequence according to SEQ ID NO: 1 (hUMOD); or a combination thereof. Other aspects provide a method for treating at least one renal disease, disorder, or condition in a subject, the method including administering to the subject an effective amount of a pharmaceutical composition of any aspect or embodiment described herein. In some embodiments of these aspects, the at least one renal disease, disorder, or condition is at least one of acute kidney injury, sepsis, transplant rejection, and chronic kidney disease. In certain embodiments, the polypeptides can be administered orally, intravenously, intraperitoneally, intramuscularly, or intradermally. In some embodiments, the effective amount of the polypeptide is between about 0.2 mg/kg and about 10.0 mg/kg. In other embodiments, the effective amount of the polypeptide is between about 0.2 mg/kg and about 3.0 mg/kg.

Another aspect described herein provides a pharmaceutical composition including a purified or isolated Tamm-Horsfall Protein (THP) polypeptide having an amino acid at least 85% identical to an amino acid sequence of SEQ ID NO: 1 (hUMOD), or a purified or isolated truncated Tamm-Horsfall Protein (THP) polypeptide comprising an amino acid sequence that is at least 85% identical to an amino acid sequence spanning from a starting position of amino acid 25 of SEQ ID NO: 1 to an ending position chosen from amino acids 130-450 of SEQ ID NO: 1; or a combination thereof. In some embodiments, the purified or isolated truncated THP polypeptide comprises an amino acid sequence at least 85% identical to an amino acid sequence chosen from SEQ ID NO: 2 (hUMOD-ΔZP), SEQ ID NO: 3 (hUMOD-EGF+ D8C), SEQ ID NO: 4 (hUMOD-EGF), and SEQ ID NO: 7. In certain embodiments, the purified or isolated truncated THP polypeptide is a chemically cleaved, enzymatically cleaved, or genetically engineered truncation of the purified or isolated THP polypeptide.

A further aspect provides an immunogenic composition including at least one immunogenic agent and a polypeptide of any aspect or embodiment described herein. Another aspect provides a method for enhancing an immune response to an immunogenic composition in a subject, the method comprising administering to the subject an effective amount of a polypeptide of any aspect or embodiment described herein.

BRIEF DESCRIPTION OF THE DRAWINGS

FIGS. 6C and 6D).

FIG. 16A) or neutrophil gelatinase-associated lipocalin (NGAL; FIG. 16B) in THP−/− mice 24 hours after ischemic reperfusion injury (IRI). Measurements were performed at baseline and after injury. Monomeric THP-treated mice had a reduction in subsequent injury compared to control (vehicle). Asterisk denotes statistical significance (p<0.05) between the two groups. N=7-8 per group.

FIGS. 16B-16C are photographs representing histological assessment of kidneys of THP−/− mice 24 hours after ischemic reperfusion injury (IRI). They photographs indicate improvement of injury compared to control (vehicle) as assessed by necrosis (N), casts (c), and dilation (D).

FIGS. 16 D-16E are graphs indicating quantitated results from FIGS. 16B and 16C (FIG. 16D) or the fold change in NGAL mRNA after treatment (FIG. 16F). Asterisk denotes statistical significance (p<0.05) between the two groups. N=7-8 per group.

FIGS. 17A-17B are photographs that indicate that injected monomeric THP reaches kidney epithelial cells. Systemic administration of THP reaches kidney proximal tubules through basolateral uptake. Intravital imaging of a kidney from a CXCR3+GFP mouse (GFP+ dendritic cells mark the kidney interstitium) before (FIG. 17A) and after (FIG. 17B) injection of 50 μg Alexa-555 labeled monomeric THP via tail vein. Within 30 minutes (FIG. 16B), THP is seen in peritubular capillaries and interstitium (arrows), at the basolateral domain of proximal tubules (arrowhead) and within tubular cells (asterisk).

FIG. 18 includes photographs that indicate that injected monomeric THP reaches kidney macrophages. The photographs depict 2-photon live microscopy of a kidney from a CXCR3+GFP mouse injected with 50 μg of Alexa 568 labeled THP (red). Myeloid cells are green due to GFP fluorescence. THP can be seen in the peri-tubular circulation and interstitium within 30 minutes after injection (arrows, faint red). However, THP is clearly concentrated and specifically localized to most myeloid cells (arrowhead). Corner inset is a snapshot of 3-D reconstruction of a z-stack using Voxx at higher magnification the area marked in the main image by the *.

DETAILED DESCRIPTION

The present disclosure relates to monomeric Tamm-Horsfall Protein (THP), modified THP (e.g., fragments), compositions including THP or a modified THP, and methods of use. In one aspect, purified or isolated polypeptides are provided. In some embodiments, the purified or isolated polypeptide is human THP (hUMOD), or a biologically active truncation thereof. In other aspects, the purified or isolated polypeptides described herein can be formulated into a pharmaceutical composition. In yet other aspects, purified or isolated peptides described herein or pharmaceutical compositions described herein can be used to treat renal diseases, disorders, and conditions in a subject. These and other aspects and embodiments are described herein.

Figure 1A:
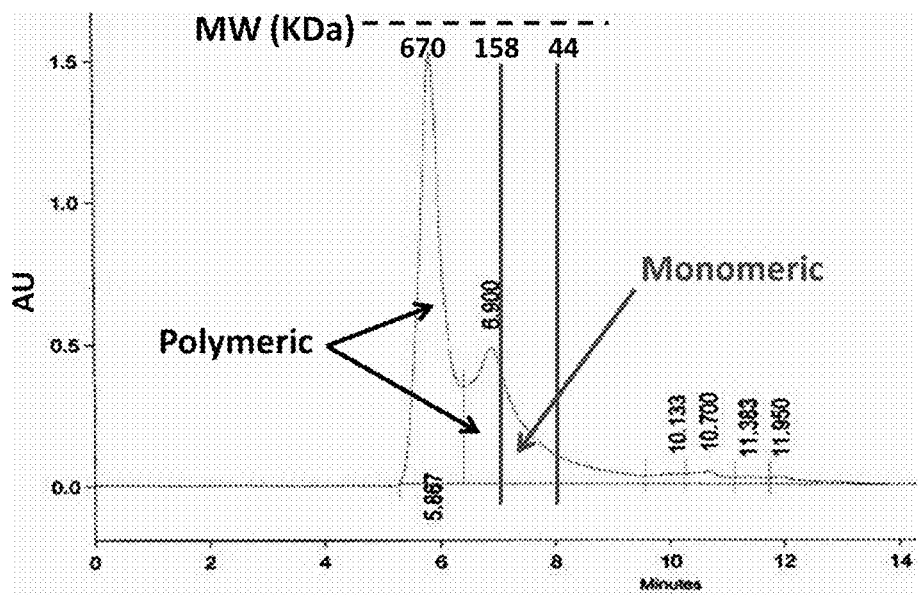
FIG. 1A is a chromatogram illustrating the proportion of polymeric vs. monomeric Tamm-Horsfall Protein (THP) found in urine.
Figure 1B:
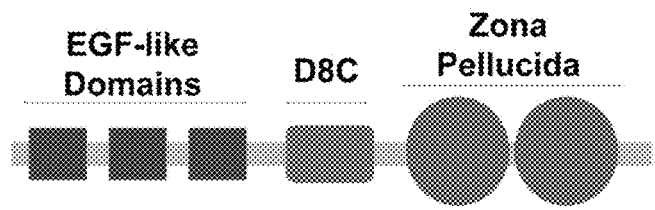
FIG. 1B is a diagram representing the structural domains of monomeric THP.
Figure 1C:
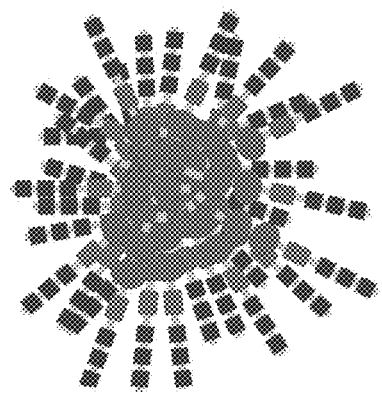
FIG. 1C is a diagram representing polymeric (i.e., aggregated) THP.

THP, also known as uromodulin, is an 80-90 kDa glycoprotein produced exclusively in the thick ascending limb (TAL) of the loop of Henle. As depicted in FIG. 1B, THP includes three Epidermal Growth Factor (EGF)-like domains, a central domain termed D8C as it contains eight conserved cysteines, and zona pellucida (ZP) domains. The protein is heavily glycosylated (~30% of its molecular weight), and is the most abundant protein excreted in the urine under physiological conditions. Within the TAL, THP is predominantly apically targeted, a process facilitated by the addition of the of a glycosylphosphatidylinositol anchor. However, THP is also released basolaterally, and has been shown to be specifically targeted to the interstitium during kidney recovery. The role of THP is generally thought to be mediated by its urinary secreted form, where it exists predominantly as a highly-aggregated polymer (see, e.g., FIGS. 1A and 1C). In certain embodiments, urinary THP is isolated and reduced to a monomeric form. Other embodiments provide C-terminal truncated THP variants. In some embodiments, the monomeric and/or truncated THP polypeptides can be used to treat renal diseases, disorders, or conditions in a subject.

In certain embodiments, a monomeric THP polypeptide can be isolated or derived from urine. The majority of urinary THP (about 85-90% is aggregated in the polymeric form, with monomeric THP (~90 kDa) accounting for only a fraction of urinary THP (about 10-15%). In some embodiments, monomeric THP can be directly isolated from urine. In other embodiments, monomeric THP can be derived from urine by isolating polymeric THP, disaggregating the isolated polymeric THP, and isolating the resultant monomeric THP (see, e.g., Example 1). In certain embodiments, the monomeric THP polypeptide is human THP (hUMOD) and has the amino acid sequence of SEQ ID NO: 1, amino acids 25-614 of SEQ ID NO: 1 (SEQ ID NO: 5), or amino acids 25-587 of SEQ ID NO: 1 (SEQ ID NO: 6). In other embodiments, the monomeric THP polypeptide can have an amino acid sequence at least 85% identical, at least 90% identical, at least 95% identical, at least 97% identical, at least 98% identical, or at least 99% identical to the amino acid sequence of SEQ ID NO: 1, amino acids 25-614 of SEQ ID NO: 1 (SEQ ID NO: 5), or amino acids 25-587 of SEQ ID NO: 1 (SEQ ID NO: 6), where the monomeric THP is biologically active.

As used herein, the term "polypeptide" is used in its broadest sense to refer to a sequence of amino acids, whether naturally occurring or of synthetic origin. The polypeptides described herein may comprise L-amino acids, D-amino acids (which are resistant to L-amino acid-specific proteases in vivo), or a combination of D- and L-amino acids. The polypeptides described herein may be chemically synthesized or produced recombinantly using recombinant DNA technology. The polypeptides may be linked to other compounds to promote an increased half-life in vivo, such as by PEGylation, HESylation, PASylation, or glycosylation. Such linkage can be covalent or non-covalent as is understood by those of skill in the art. The polypeptides may be linked to any other suitable linkers, including but not limited to any linkers that can be used for purification or detection (such as, e.g., FLAG or His tags).

In other embodiments, a monomeric THP polypeptide can be a biologically active truncation of the monomeric THP isolated or derived from urine, or a truncation of the amino acid sequence of SEQ ID NO: 1. In some embodiments, the truncated THP polypeptide has an amino acid sequence that spans from amino acid 25 of SEQ ID NO: 1 to an ending position chosen from any one of amino acids 120 to 450 of SEQ ID NO: 1. In certain embodiments, the ending position is chosen from any one of amino acids 140 to 440 of SEQ ID NO: 1. In yet other embodiments, the ending position is an amino acid chosen from amino acid 149, 289, 337, or 434 of SEQ ID NO: 1. In some embodiments, the biologically active truncation of the monomeric THP can be a polypeptide having the amino acid sequence of SEQ ID NO: 7. In certain embodiments, the truncated THP polypeptide can have an amino acid sequence at least 85% identical, at least 90% identical, at least 95% identical, at least 97% identical, at least 98% identical, or at least 99% identical to the amino acid sequence of SEQ ID NO: 1 to which the truncated THP polypeptide corresponds, where the truncated THP polypeptide is biologically active. For example, a truncated THP polypeptide can include an amino acid sequence at least 85% identical to amino acids 25-310 of SEQ ID NO: 1. Truncated THP polypeptides described herein can be generated by, for example, chemical cleavage of a monomeric THP polypeptide, enzymatic cleavage of a monomeric THP polypeptide, or by recombinant protein generation methods (see, e.g., Example 2).

In some embodiments, the truncated THP polypeptide can be hUMOD-ΔZP, hUMOD-EGF+D8C, or hUMOD-EGF. These truncations were designed to reduce the overall molecular weight relative to full-length monomeric human THP (hUMOD; ~90 kDa). The polypeptide hUMOD-ΔZP is a truncation of hUMOD, where the C-terminal domain encoding the zona pellucida (ZP) domains is removed. hUMOD-ΔZP has the amino acid sequence of SEQ ID NO: 2. The polypeptide hUMOD-EGF+D8C is a C-terminal truncation of hUMOD up to the D8C domain. hUMOD-EGF+D8C has the amino acid sequence of SEQ ID NO: 3. The polypeptide hUMOD-EGF is a C-terminal truncation of hUMOD up to the three EGF domains of hUMOD. hUMOD-EGF has the amino acid sequence of SEQ ID NO: 4. In certain embodiments, the truncated THP polypeptide includes an amino acid sequence of one of SEQ ID NO: 2, SEQ ID NO: 3, or SEQ ID NO: 4. In other embodiments, the truncated THP polypeptide has the amino acid sequence of SEQ ID NO: 7. In yet other embodiments, the truncated THP polypeptide includes an amino acid sequence that is at least 85% identical, at least 90%, at least 95% identical, at least 97% identical, at least 98% identical, or at least 99% identical to the amino acid sequence of one of SEQ ID NO: 2, SEQ ID NO: 3, SEQ ID NO: 4, or SEQ ID NO: 7, where the truncated THP polypeptide is biologically active.

Other aspects provide an isolated polynucleotide encoding a THP polypeptide of any aspect or embodiment described herein. The encoded THP polypeptide can be a monomeric THP polypeptide or a truncated THP polypeptide. The isolated polynucleotide may be an RNA sequence or a DNA sequence. As used herein, "isolated nucleic acids" are those that have been removed from their normal surrounding polynucleotide sequences in the genome or in cDNA sequences. In some embodiments, the polynucleotide can have a nucleic acid sequence that encodes a polypeptide having an amino acid sequence that is at least 85% identical, at least 90%, at least 95% identical, at least 97% identical, at least 98% identical, or at least 99% identical to the amino acid sequence of one of SEQ ID NO: 1, amino acids 25-614 of SEQ ID NO: 1 (SEQ ID NO: 5), amino acids 25-587 of SEQ ID NO: 1 (SEQ ID NO: 6), SEQ ID NO: 2, SEQ ID NO: 3, SEQ ID NO: 4, or SEQ ID NO: 7, where the encoded polypeptide is biologically active. In some embodiments the isolated polynucleotides can include one or more additional sequences useful for promoting expression and/or purification of the encoded protein. For example, polyA sequences, sequences encoding epitope tags, export signals, secretory signals, nuclear localization signals, plasma membrane localization signals, or other signal sequence, and combinations thereof, may be included in an isolated polynucleotide.

Another aspect provides nucleic acid expression vectors that include a polynucleotide described herein. In some embodiments the polynucleotide is operably linked to a suitable control sequence, such as, for example, a promoter, polyadenylation signal, termination signal, or ribosome binding site. Expression vectors include those vectors that operably link a polynucleotide coding region or gene to any control sequences capable of effecting expression of the gene product. In some embodiments, the control sequence (e.g., a promoter sequence) is not contiguous with the polynucleotide sequence, so long as the control sequence functions to direct the expression of the polynucleotide. A nucleic acid expression vector can be of any type known in the art, including but not limited to plasmid and viral-based expression vectors. The control sequence used to drive expression of the polynucleotide described herein in a mammalian system can be constitutive (e.g., driven by a constitutive promoter such as, for example, CMV, SV40, RSV, actin, EF), or inducible (e.g., driven by an inducible promoter such as, for example, tetracycline-inducible promoters). Methods for constructing expression vectors for use in polypeptide expression systems (i.e., mammalian cells) are well known in the art, as are methods for expressing proteins therein and isolating and purifying the expressed polypeptide, and can be accomplished via standard techniques.

Another aspect provides recombinant host cells including a nucleic acid expression vector described herein. Host cells can be either transiently or stably transfected or transduced by known methods, such as standard bacterial transformations, calcium phosphate co-precipitation, electroporation, and liposome mediated-, DEAE dextran mediated-, polycationic mediated-, or viral-mediated transfection. Also provided are methods of producing a polypeptide described herein, wherein the methods generally include i) culturing a recombinant host cell described herein under conditions conducive to the expression of the polypeptide, and optionally ii) recovering the expressed polypeptide. The expressed polypeptide can be recovered from the cell-free extract, cell pellet, or recovered from the culture medium. Methods to purify recombinantly-expressed polypeptides are well known in the art.

Another aspect provides pharmaceutical compositions including one or more polypeptides, polynucleotides, nucleic acid expression vectors, or recombinant host cells described herein, or a combination thereof, and a pharmaceutically acceptable carrier. In some embodiments, the pharmaceutical compositions include at least one polypeptide described herein and a pharmaceutically acceptable carrier. The pharmaceutical compositions can be used, for example, in the methods described herein. In some embodiments, a pharmaceutical composition can also include other elements, such as, for example, a lyoprotectant (e.g., sucrose, sorbitol, or trehalose), a surfactant (e.g., polysorbate-20, -40, -60, -65, -80, -85, sorbitan monolaurate, sorbitan monopalmitate, etc., and combinations thereof), a bulking agent (e.g., glycine), a tonicity adjusting agent (e.g., sucrose, sorbitol, glycine, methionine, mannitol, dextrose, inositol, sodium chloride, arginine, arginine hydrochloride), a stabilizer (e.g., sucrose, sorbitol, glycine, methionine, glycine, inositol, sodium chloride, arginine, arginine hydrochloride), a preservative (e.g., benzalkonium chloride, benzethonium, chlorohexidine, phenol, benzyl alcohol, benzoic acid, etc., and mixtures thereof), a buffer (e.g., a Tris buffer, histidine buffer, phosphate buffer, citrate buffer, acetate buffer), of a combination thereof.

In some embodiments, a polypeptide, polynucleic acid, nucleic acid expression vector, or recombinant host cell can be the sole active agent in the pharmaceutical composition. In other embodiments, the composition can include one or more other active agents suitable for an intended use.

In some embodiments, pharmaceutical compositions described herein include at least one polypeptide described herein and a pharmaceutically acceptable carrier, diluent, or excipient. These compositions can be prepared in a manner well known in the pharmaceutical arts, and can be administered by any suitable route, such as, for example, intravenously, intraperitoneally, intramuscularly, or subcutaneously. In some embodiments a pharmaceutical composition is administered intravenously or orally. The pharmaceutical compositions can be any suitable form, including but not limited to tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

In certain embodiments, a pharmaceutical composition can include one or more purified or isolated truncated THP polypeptides described herein. In some other embodiments, a pharmaceutical composition can include one or more full-length monomeric THP polypeptides described herein (e.g., a polypeptide with an amino acid sequence at least 85% identical to SEQ ID NO: 1, amino acids 25-614 of SEQ ID NO: 1 (SEQ ID NO: 5), or amino acids 25-587 of SEQ ID NO: 1 (SEQ ID NO: 6)) and does not include truncated THP polypeptides.

Another aspect provides methods for treating at least one renal disease, disorder, or condition, where the method includes administering to a subject one or more polypeptides described herein. Another aspect provides methods for preventing or reducing the symptoms of at least one renal disease, disorder, or condition, where the method includes administering to a subject at risk of developing a renal disease, disorder, or condition one or more polypeptides described herein. In some embodiments, the methods for treating include administering to the subject at least one polypeptides of SEQ ID NO: 1, amino acids 25-614 of SEQ ID NO: 1 (SEQ ID NO: 5), amino acids 25-587 of SEQ ID NO: 1 (SEQ ID NO: 6), SEQ ID NO: 2, SEQ ID NO: 3, and SEQ ID NO: 4, and SEQ ID NO: 7. In some embodiments, poly peptides of a single amino sequence are administered. In other embodiments, two or more polypeptides having different amino acid sequences are administered. The methods described herein may thus include administering polypeptides of at least one of SEQ ID NO: 1, amino acids 25-614 of SEQ ID NO: 1 (SEQ ID NO: 5), amino acids 25-587 of SEQ ID NO: 1 (SEQ ID NO: 6), SEQ ID NO: 2, SEQ ID NO: 3, SEQ ID NO: 4, SEQ ID NO: 7, or a combination thereof.

In some embodiments, the one or more administered polypeptides include an amino acid sequence at least 85% identical to an amino acid of at least one of SEQ ID NO: 1, amino acids 25-614 of SEQ ID NO: 1 (SEQ ID NO: 5), amino acids 25-587 of SEQ ID NO: 1 (SEQ ID NO: 6), SEQ ID NO: 2, SEQ ID NO: 3, and SEQ ID NO: 4, as described herein.

In other embodiments, the one or more administered polypeptides include an amino acid sequence that is at least 85% identical to an amino acid sequence spanning from a starting position of amino acid 25 of SEQ ID NO: 1 to an ending position chosen from amino acids 130-450 of SEQ ID NO: 1, or a combination thereof, as described herein.

In certain embodiments, the polypeptides can be administered to the subject as part of a pharmaceutical composition described herein.

In another aspect, polypeptides described herein can be used to modulate an immune response. For example, the peptides can be used to inhibit inflammatory signaling in the kidney. The polypeptides can also be used to activate renal macrophage or increase the number of renal macrophage. These effects may be beneficial in diseases, disorders and conditions not limited to those associated with THP deficiency. For example, treatment with the polypeptides described herein may be beneficial in inflammatory conditions such as sepsis. The polypeptides may also be used to reduce the risk of, or prevent, kidney transplant rejection by triggering proliferation and activation of beneficial renal macrophage, as well as limiting inflammation.

Polypeptides described herein may also provide systemic benefits by inhibiting inflammatory signaling and/or triggering proliferation and activation of macrophage outside of the kidney. This is supported in that a predominant phenotype in THP-associated diseases is interstitial inflammation and subsequent fibrosis.

In another aspect, polypeptides described herein can be used to boost or improve an immune response in a subject to, for example, an immunogenic composition such as a vaccine composition. As demonstrated in the examples, polypeptides disclosed herein can inhibit inflammatory signaling and cause proliferation and activation of renal macrophage. The polypeptides can be administered as a vaccine adjuvant, and can be administered before, after, or concurrently with a vaccine. In some embodiments, the polypeptide can be incorporated into a vaccine composition. In some embodiments, polypeptides can be used to boost or improve a systemic immune response to an antigen. In other embodiments, the polypeptides can be used to boost or improve a kidney-specific immune response to an antigen.

In some embodiments, a polypeptide described herein can be administered to a subject to protect the kidney from damage by a vaccine composition. In certain embodiments, the polypeptide is administered to a subject having a kidney transplant. In such embodiments, the polypeptides can be administered before, after, or concurrently with a vaccine composition to protect the kidney from damage caused by inflammation. In certain embodiments, the polypeptide is incorporated into a vaccine composition.

Renal diseases, disorders, and conditions contemplated herein include, but are not limited to, acute kidney injury, sepsis, transplant rejection, and chronic kidney disease. Conditions such as acute kidney injury and chronic kidney disease are associated with a THP deficiency (see, e.g., FIGS. 2A-2D and Example 3). As demonstrated in the Examples, it is now shown that administering monomeric THP following acute kidney injury can protect from worsening injury and improve resulting injury. Further, monomeric THP is demonstrated to initiate or modulate immune responses in a subject, including inhibiting inflammatory signaling in the kidney, activating renal macrophage, and increasing the number of renal macrophage. By administering polypeptides disclosed herein to modify an immune response in the kidney, conditions such as sepsis and transplant rejection can be treated.

As used herein, "treating" means accomplishing one of the following: i) reducing the severity of a renal disease, disorder, or condition; ii) limiting or preventing development of symptoms characteristic of a renal disease, disorder, or condition; iii) inhibiting worsening of symptoms characteristic of a renal disease, disorder, or condition; iv) improving symptoms characteristic of a renal disease, disorder, or condition; v) limiting or preventing recurrence of a renal disease, disorder, or condition in a subject previously symptomatic for the disease, disorder, or condition; and vi) limiting development of a renal disease, disorder, or condition in a subject at risk of developing the renal disease, disorder, or condition, or not yet showing clinical signs of the renal disease, disorder, or condition.

Subjects to be treated according to the methods described herein can be any subject suffering from a renal disease, disorder, or condition, or at risk of developing a renal disease, disorder, or condition, including human subjects. The subject may be one already suffering from symptoms, or one who is asymptomatic.

As used herein, an "effective amount" refers to an amount of the polypeptide that is effective for treating a renal disease, disorder, or condition. The polypeptides are typically formulated as a pharmaceutical composition, such as those described herein, and can be administered by any suitable route.

Dosage regimens can be adjusted to provide the optimum desired response (e.g., a therapeutic or prophylactic response). A suitable dosage range may be, for example, from about 0.2 mg/kg to about 10 mg/kg body weight; alternatively, it may be from about 0.2 mg/kg to about 3.0 mg/kg. In certain embodiments, pharmaceutical compositions described herein can be administered in a single dose. In other embodiments, the compositions are administered in two or more doses. Where multiple doses are administered, administration may occur in one day, or over two or more days, and can include continuous infusion. Multiple doses and/or continuous infusion can be beneficial to maintain consistently elevated serum levels of monomeric THP or a truncated THP.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this invention, and without departing from the spirit and scope thereof, can make various changes and modifications of the invention to adapt it to various usages and conditions.

Example 1—Monomeric THP

The prevailing paradigm remains that the major functions of THP are mediated by its urinary secreted form. Most, if not all, functional studies have employed the urinary secreted form of THP, isolated directly from urine, which forms a protein aggregate having a molecular weight of $1-10 \times 10^6$ Da. It is now described and reported herein that monomeric THP treats AKI in mice, protects from worsening injury, and increases the number of macrophages in the kidney of THP−/− mice, and alters their activation state.

Monomeric THP was purified from urinary THP. A starting volume of 1.5 L of human urine was brought to 0.58M NaCl. After incubation at 4° C. for 16 h, insoluble material was collected by centrifugation for 30 min at 17,000×g at 4° C. The pellet was then resuspended in 0.5 L sterile deionized water and re-precipitated in the presence of 0.58M NaCl. This was repeated twice, and a final 50 ml of THP pellet suspension was dialyzed exhaustively against sterile deionized water, using SnakeSkin dialysis tubing of 10K MWCO. Typical yield of precipitated human urinary THP was 15 mg.

Dialyzate was then concentrated to 20 ml using 15 ml Amicon Ultra concentrators with MWCO of 10K. Urea was added to the dialysate to 8M final, and the suspension was incubated for 16 h at 4° C. with tumbling in order to isolate monomeric THP from the THP aggregated multimers. The 8M THP suspension was then concentrated to 1 ml in the Amicon concentrators, and loaded onto a Superdex 200 Size Exclusion Chromatography (SEC) column pre-equilibrated with 30 mM phosphate buffer, pH 6.8 containing 2M urea. Chromatography was carried out at the flow rate of 0.65 ml/min, controlled by peristaltic pump. Fractions were collected every 2 min. Fractions were analyzed for protein UV content using NanoVue spectrophotometer, and chromatograms generated by plotting fraction number (or retention time) versus protein UV (mg/ml).

Figure 20:
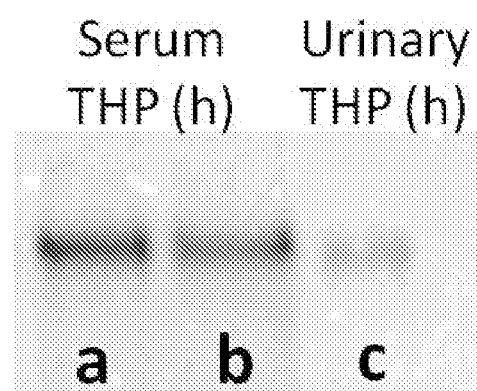
FIG. 20 is a photograph of a blot illustrating immuno-precipitation of THP from human serum. Western blot analysis was performed for THP in human serum (lane A and lane B) after immuno-precipitation. Lane C is urinary THP, which was used as control.
Figure 21:
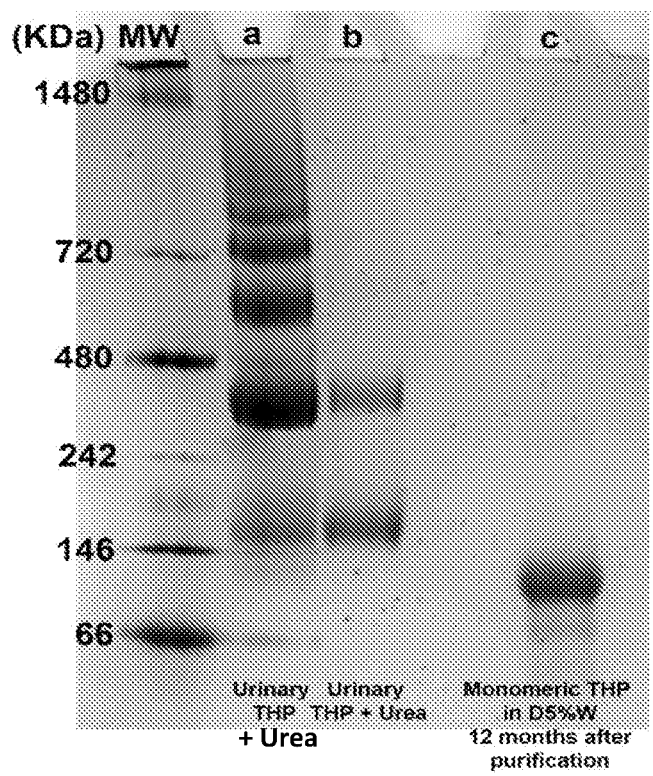
FIG. 21 is a photograph of a native gel that indicates the stability of monomeric THP. Monomeric THP remains stable in D5W up to at least 1 year after purification (lane c). Lanes a and b represent urinary THP+urea before size-exclusion chromatography (SEC) purification in various aggregated forms. Molecular weight markers are shown in the left most lane.

Aliquots from the peak fractions were then run on Native PAGE (4-16% gel; 120 minutes at 150V. Fractions containing true monomeric THP were then pooled and buffer-exchanged to 5% dextrose solution using 5 ml Zeba Spin desalting columns with 7K MWCO. The monomeric THP solution (~1.5 mg total at a protein concentration of about 1 mg/ml) was then kept at 4° C. until further use. Monomeric THP was periodically checked on Native PAGE to ensure its stability in the monomeric form. In such formulation with 5% dextrose, the monomeric form of THP is stable for more than 1 year (FIG. 20).

The procedure described above yields about 1 mg of monomeric THP from 10 mg of urinary THP.

Figure 19:
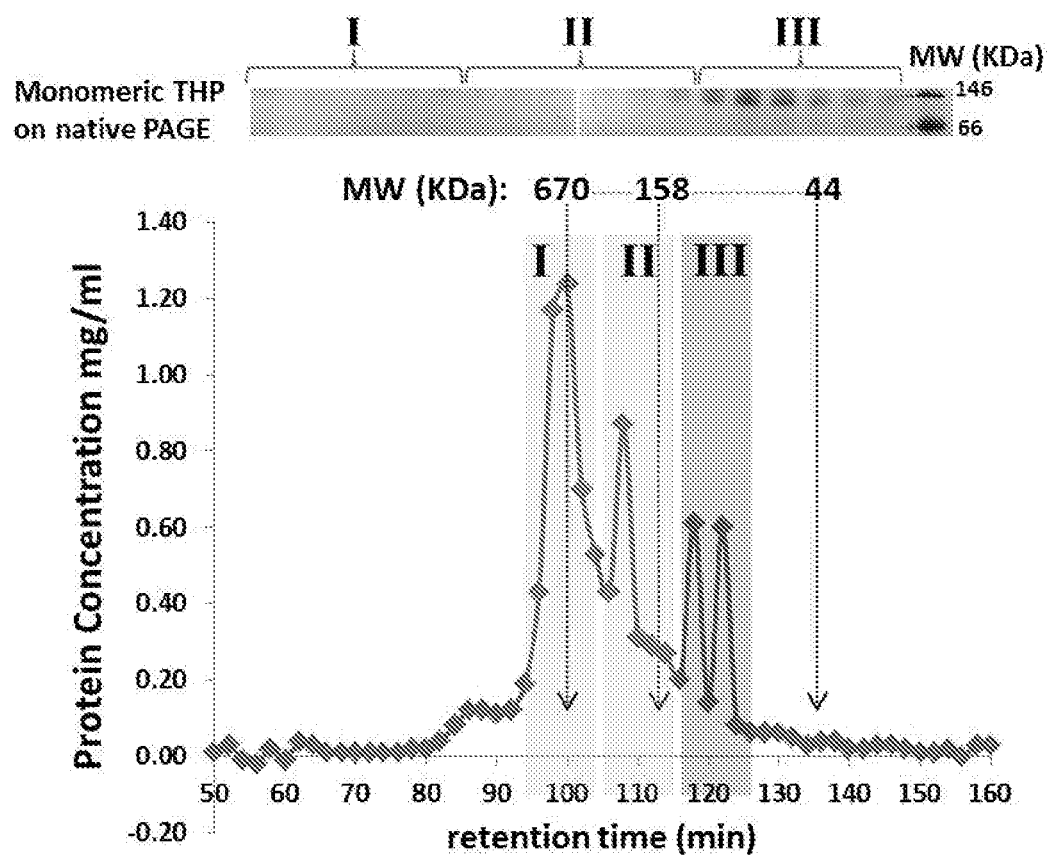
FIG. 19 represents preparative gel filtration chromatography of urinary THP. Urinary THP was treated with 8M urea, and then chromatographed on a Superdex 200 gel filtration column in 2M urea buffer. THP fractions were collected and 3 major peaks were observed. Monomeric THP was expected to be in peak III based on molecular weight. This was verified by native gel electrophoresis on all recovered fractions.

As indicated in FIG. 19, the two forms of THP (urinary and circulating) are the same, despite urinary THP existing predominantly a highly aggregated polymer.

Example 2—THP Truncations

Because of its relatively high molecular weight, several truncations of THP were designed. These include hUMOD-ΔZP (SEQ ID NO: 2), wherein the C-terminal domain encoding the zona pellucida (ZP) domains is removed; hUMOD-EGF+D8C (SEQ ID NO: 3), a C-terminal truncation up to the D8C domain; and hUMOD-EGF (SEQ ID NO: 4), a C-terminal truncation up to the 3 EGF domains. The C-terminal deletion mutants were synthesized and subcloned into pcDNA3.1 for heterologous expression in mammalian HEK293 cells. The genes were synthesized using optimal human codons, using human IgG kappa light chain signal peptide for enhanced secretion.

Figure 22:
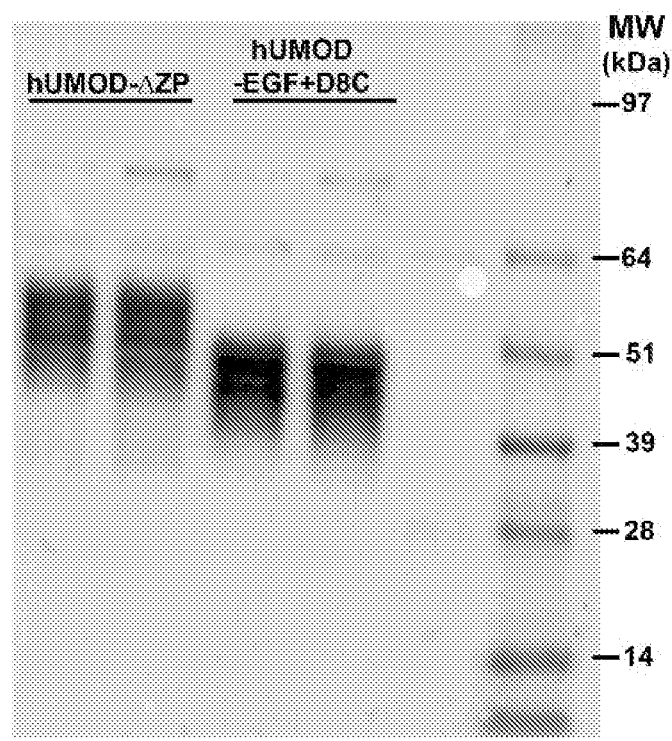
FIG. 22 is a photograph of a Western Blot illustrating expression of hUMOD-ΔZP and hUMOD-EGF+D8C in HEK-293 cells.

As indicated by FIG. 22, hUMOD-ΔZP (SEQ ID NO: 2) and hUMOD-EGF+D8C (SEQ ID NO: 3C) constructs were successfully transfected and expressed in HEK-293 cells. Media was collected at days 4 and 5, subjected to SDS PAGE, and probed with anti-THP antibody.

Figures 2A, 2B:
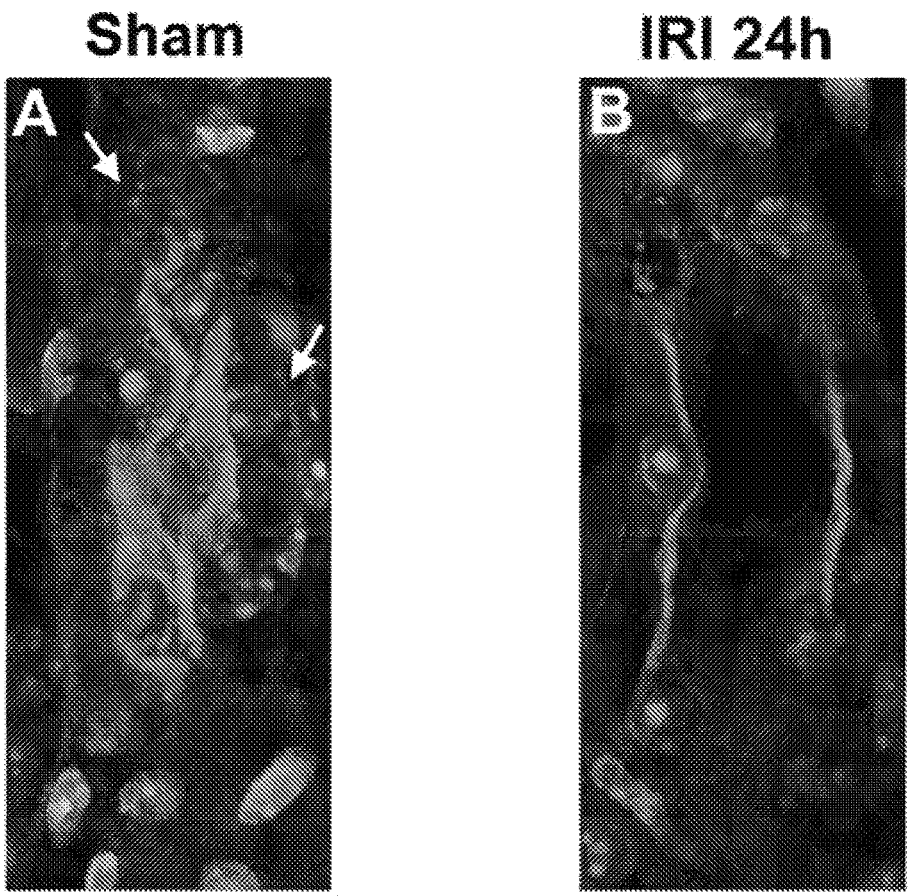
FIGS. 2A-2B are photographs illustrating THP expression in the thick ascending limb in sham control (FIG. 2A) and following AKI initiated by ischemia reperfusion injury (IRI) (FIG. 2B). THP expression decreases both at the apical and basolateral domains (arrow).
Figure 2C:
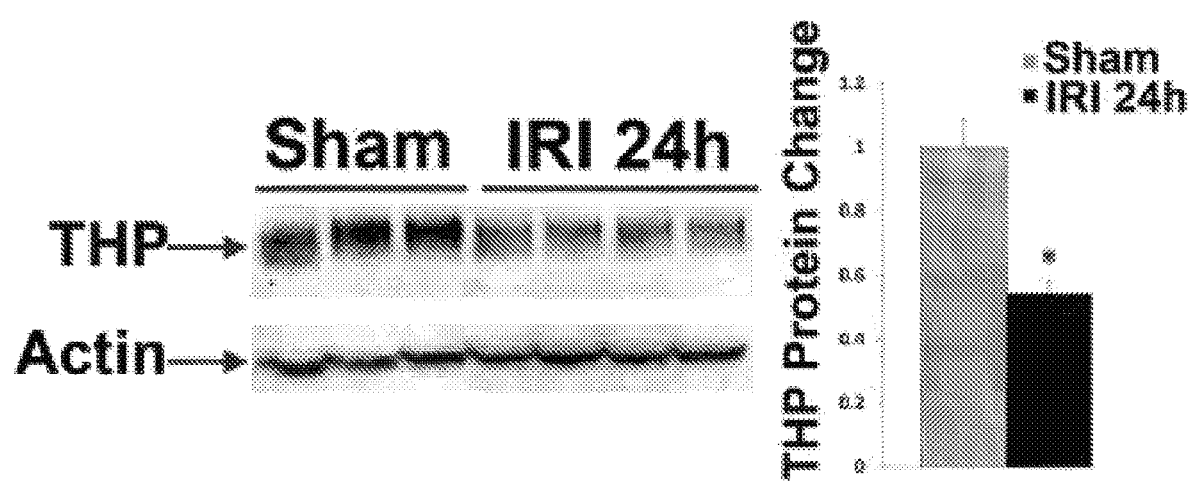
FIGS. 2C-2D are graphs indicating decreased THP polypeptide (FIG. 2C) and mRNA (FIG. 2D) following acute kidney injury (AKI). Downregulation of THP was proportional to the degree of injury.
Figure 2D:
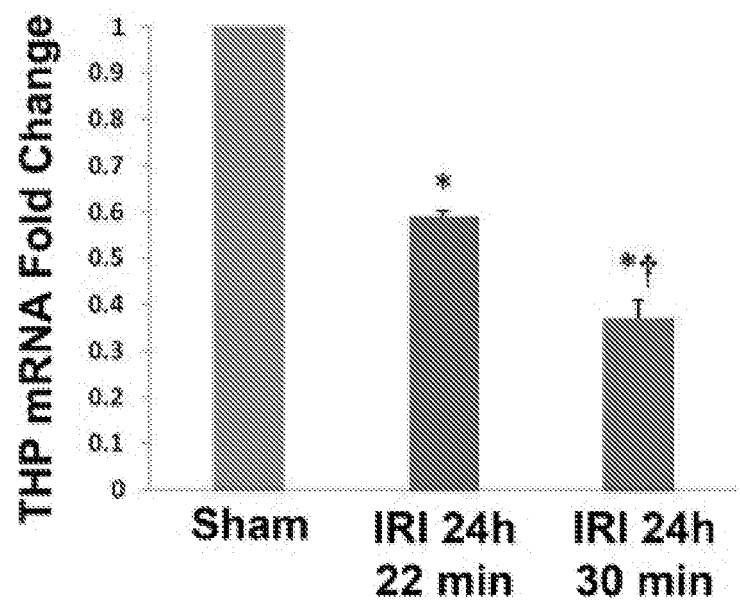
Figure 2E:
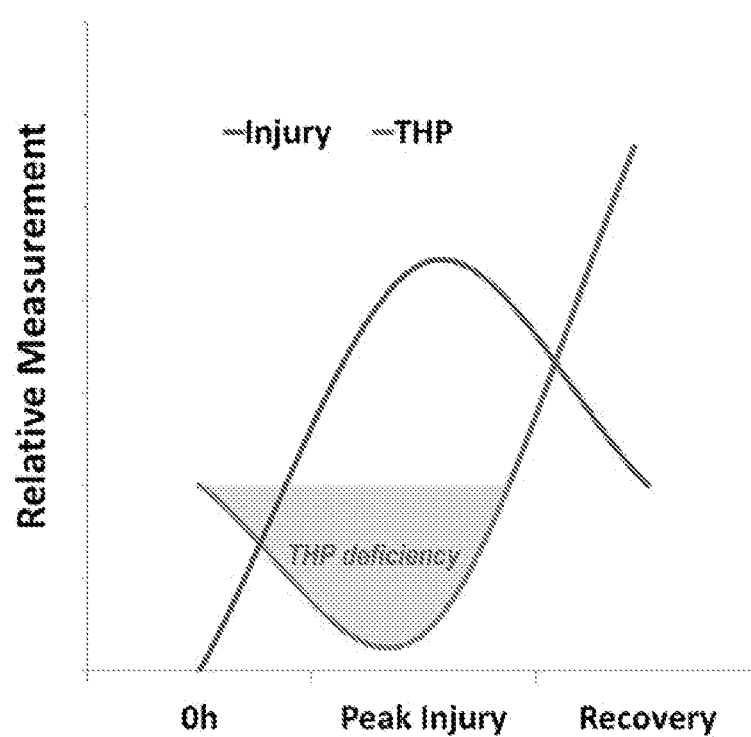
FIG. 2E is a graph comparing THP levels relative to injury progression. The graph indicates that recovery from AKI is associated with increased levels of THP.

Example 3—Treatment of Diseases, Disorders, and Conditions Associated with THP Deficiency As depicted in FIGS. 2A-2D, acute kidney injury (AKI) leads to a state of significant THP deficiency, at both the protein and mRNA levels, which is proportional to the degree of injury. As indicated by a comparison of FIG. 2A (sham control) and FIG. 2B (following AKI), THP expression was decreased in the apical and basolateral domains (see arrows of FIG. 2A) following AKI initiated by ischemic reperfusion injury (IRI). FIG. 2B indicates a lack of expression in these domains following AKI. The decrease in THP expression following AKI was confirmed by Western blot analysis (see FIG. 2C). This downregulation in protein levels may occur at the level of gene expression, as THP mRNA levels also decreased following AKI. As depicted in FIG. 2E, recovery from AKI is associated with increased levels of THP.

Monomeric THP and truncations thereof were shown to protect from worsening kidney injury following AKI, and can be used to treat AKI or protect against its development.

Figure 14:
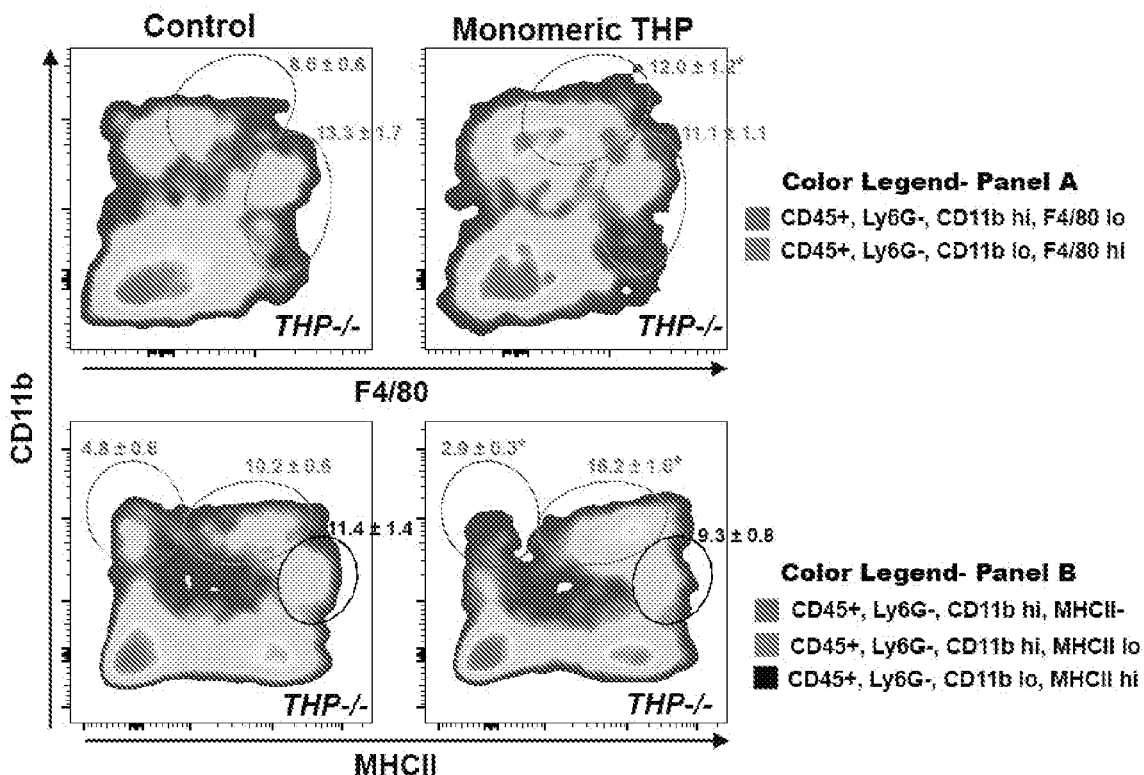
FIG. 14 depicts flow cytometry results, which indicate that treatment of THP−/− mice with monomeric THP increases the number of macrophages and their activation state. The plots indicate flow cytometry of kidneys from THP−/− mice treated with vehicle or monomeric THP administered at a dosage of 10 μg/mouse intraperitoneal daily for 6 days (n=6 per group). The numbers are percentages of cells out of total number of CD45+ cells. * denotes statistical significance between the two groups. There is significant increase in macrophage numbers observed in the top two panels. The bottom two panels indicate that THP causes a shift of macrophages towards an active state (from 11b hi, MHCII negative, to 11b hi, MHCII low). Dendritic cells (11b low, F4/80 hi, MHCII hi) are unaffected.

THP−/− mice were treated intraperitoneally with 10 μg/mouse monomeric THP or vehicle daily for 6 days. Following 6 days of treatment with monomeric THP, there was a significant increase in macrophage number (FIG. 14). In addition to increasing the numbers of renal macrophage in THP−/− mice, monomeric THP also caused a shift in macrophage towards an active state. Dendritic cells were unaffected.

Figure 15:
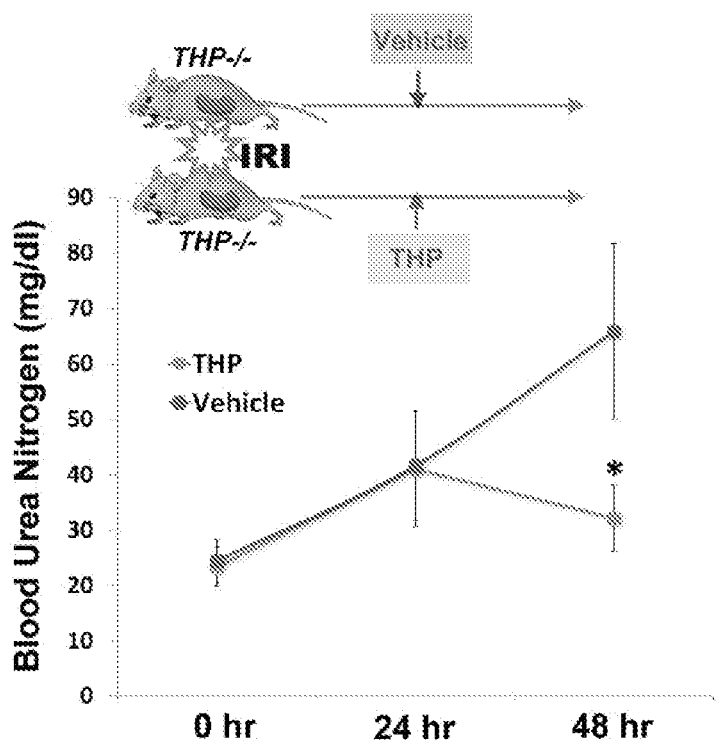
FIG. 15 is a graph that indicates that administration of monomeric THP after IRI protects from worsening injury. THP−/− mice were treated 24 h after IRI with THP or vehicle. BUN was measured at baseline and daily after injury. THP-treated mice had a correction of the course of AKI towards recovery at 48 h. Vehicle-treated mice had worsening injury. * denotes statistical significance (p<0.05) between the two groups. N=5-6 per group.
Figure 16A:
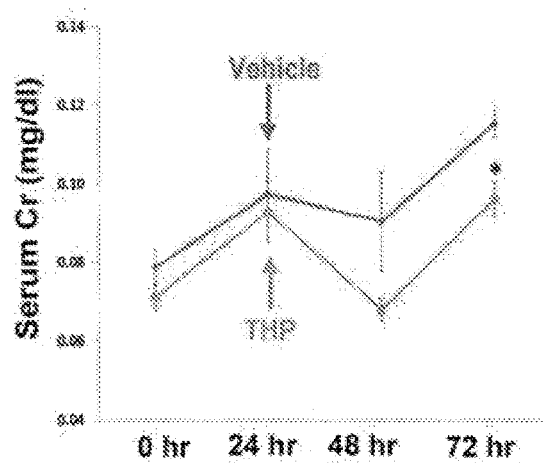
FIGS. 16A-16B are graphs indicating measured serum creatinine (Cr.
Figure 16B:
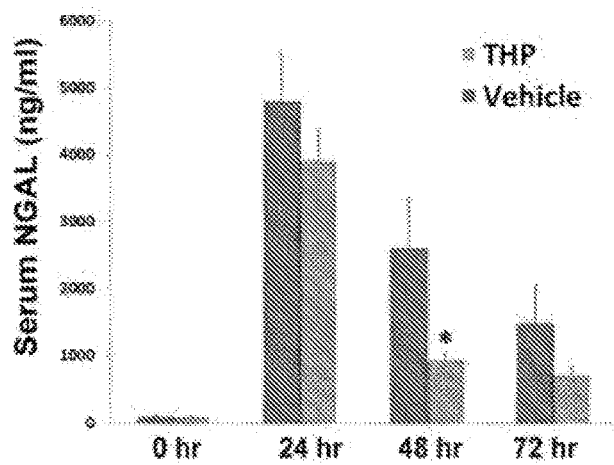
Figure 16C:
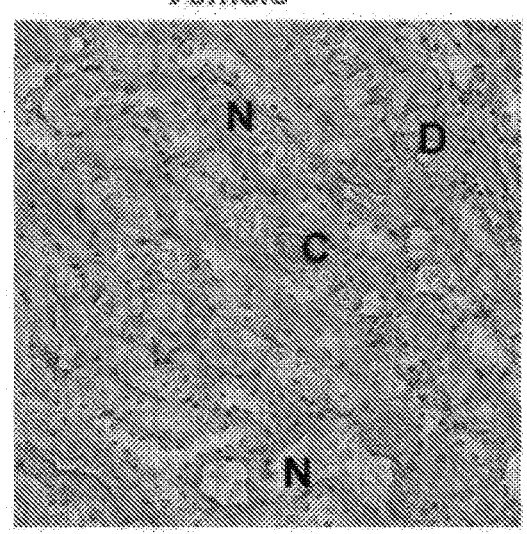
Figure 16D:
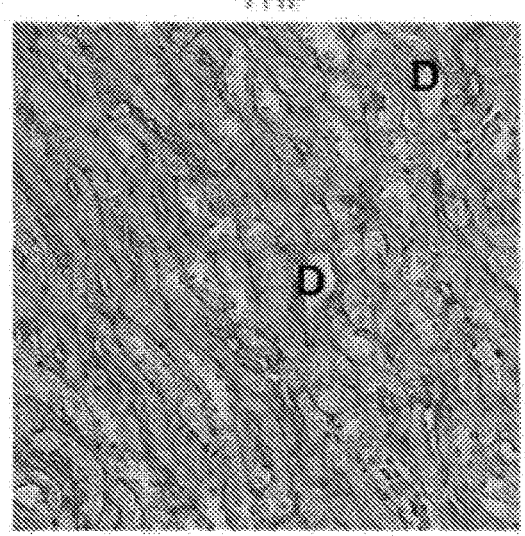
Figure 16E:
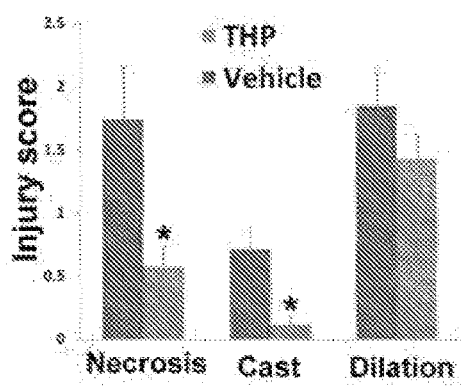
Figure 16F:
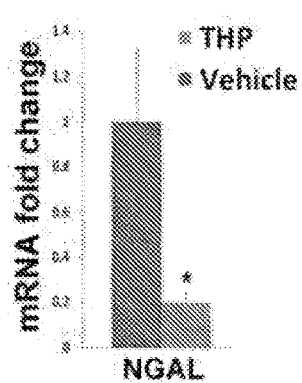

THP−/− mice are prone to acute kidney injury. 24 h following induction of AKI in THP−/− mice by renal ischemia reperfusion injury, mice were treated intraperitoneally with 20 μg/mouse monomeric THP or vehicle. Blood urea nitrogen (BUN) was measured at baseline and daily after injury. The two groups had a comparable degree of injury, as measured by BUN levels at 24 h post injury. Monomeric THP-treated mice had a correction of the course of AKI towards recovery at 48 h post injury, when kidney function started to improve (FIG. 15). Vehicle treated mice had worsening injury, which is typical of THP−/− mice at that time point. The reduction in subsequent injury in THP-treated mice is further evidenced by the reduction in serum creatinine levels following AKI (FIG. 16A) and a reduction in serum NGAL levels (FIG. 16B), both markers of renal function/damage. Histological assessment at 72 hours also indicated improvement of injury (FIGS. 16C-16D), as assessed by observed necrosis (N), casts (C), and dilation (D). This improvement is quantitated in FIG. 16E. Further, NGAL mRNA was significantly reduced in THP treated mice compared to vehicle treated mice (FIG. 16F). These data indicate that monomeric THP can treat AKI.

To demonstrate the ability of monomeric THP to reach either renal macrophage or S3 proximal tubule epithelium, monomeric THP was labeled with Alexa 568 and injected into CXCR3+GFP mice (FIGS. 17-18). 50 μg of Alexa 568-labeled monomeric THP was observed in peri-tubular circulation and interstitium within 30 minutes after injection. However, monomeric THP was clearly concentrated and specifically localized to most myeloid cells. Alexa 568-labeled monomeric THP was similarly detected in the peritubular circulation and interstitium 30 minutes post systemic injection. Monomeric THP was observed at the basolateral domain of proximal tubules and within tubular cells, demonstrating that the monomeric THP also reached kidney epithelial cells.

Monomeric THP can also be used to treat THP-associated diseases other than AKI, such as CKD. CKD is also characterized by a state of THP deficiency. Several studies have shown that THP levels in the urine and in the serum decrease with advanced CKD and tubular atrophy. Monomeric THP can be used to improve the inflammatory phenotype observed in patients with CKD by mechanisms described herein. This improvement may have an effect on cardiovascular health and prevent further deterioration of kidney function.

In methods for treating a subject, a therapeutically effective amount of a pharmaceutical composition including about 0.2 mg/kg to about 10.0 mg/kg monomeric THP or a biologically active truncated THP can be administered to a subject suffering from a disease characterized by altered THP levels, such as acute kidney injury (AKI) and chronic kidney disease (CKD). Treatment using the pharmaceutical composition can result in increased renal macrophage numbers and activation levels, and/or can inhibit inflammatory signaling pathways, thereby treating or ameliorating the THP-associated disease in the subject.

Where the subject has or is at risk of having an AKI, treatment with a therapeutically effective amount of the pharmaceutical composition can improve kidney function and reduce kidney injury following AKI.

Where the subject presents with CKD, treatment with the therapeutically effective amount of the pharmaceutical composition can improve the inflammatory phenotype with CKD and prevent deterioration of kidney function.

Example 4—Effects of THP in the Kidney

Figure 3:
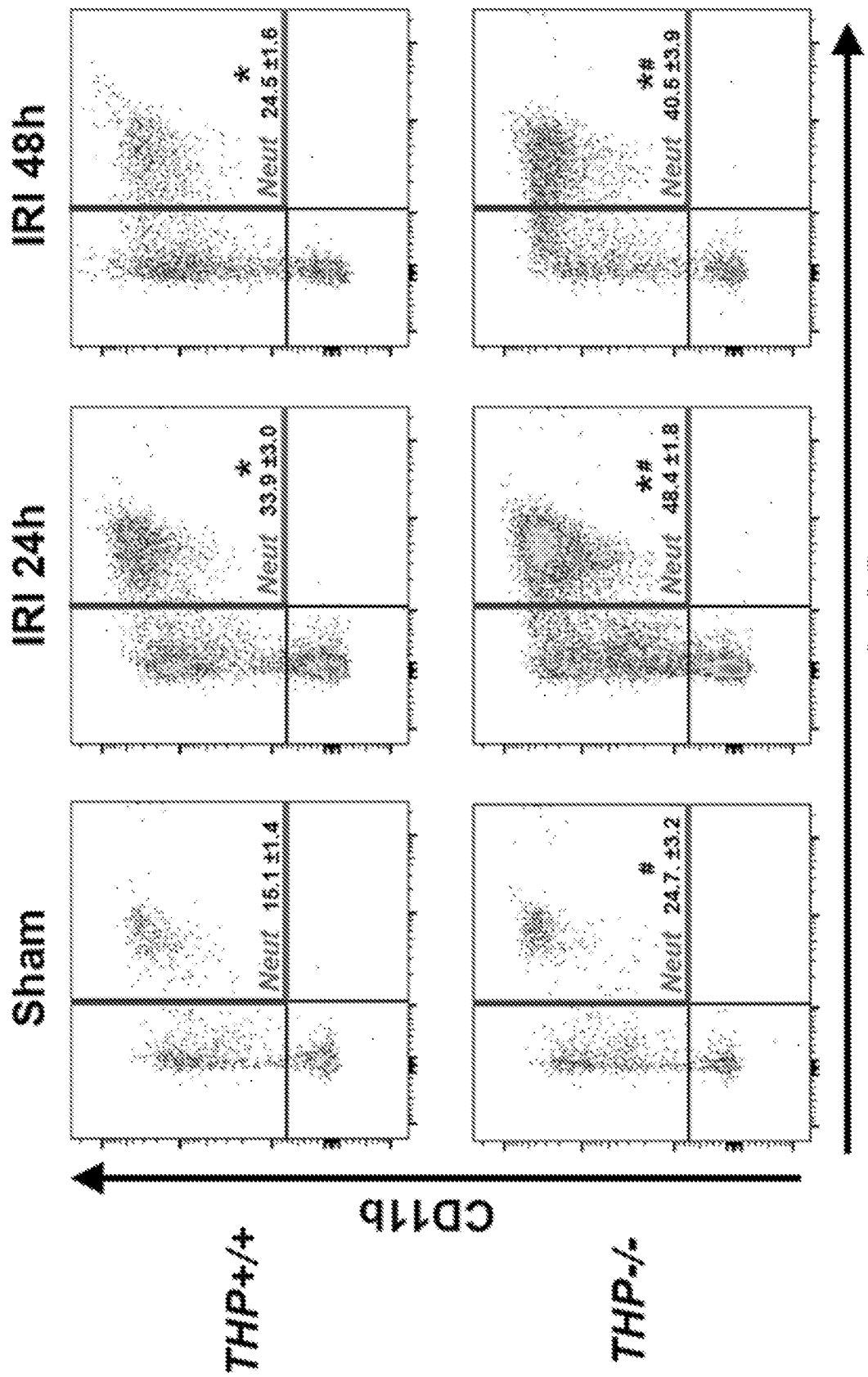
FIG. 3 is a series of scatter plots representing flow cytometry results for neutrophils following AKI in THP-/- and THP+/+ mice. Scatter plots show CD45+ cells gated for CD11b and Ly6G after sham or ischemia-reperfusion injury (IRI) with 24 or 48 hours recovery (n=5/group/time point). Neutrophils are defined as CD11b+, Ly6G+. * and # denote statistical significance vs. sham and THP+/+, respectively ($p<0.05$).
Figure 4A:
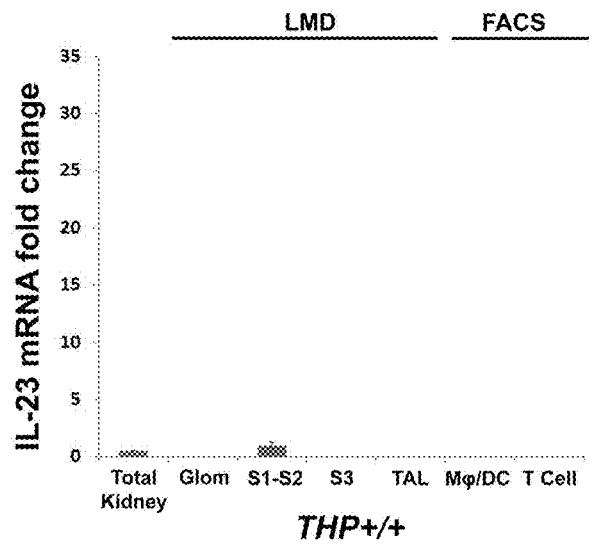
FIGS. 4A-4B are bar graphs indicating the source of IL-23 in the uninjured kidney using laser micro-dissection (LMD) and fluorescence-activated cell sorting (FACS). The bar graphs indicate IL23 mRNA levels in specific cell types from THP+/+(FIG. 4A) and THP-/- (FIG. 4B) kidneys. Total kidney from THP-/- was used as a reference sample. # denotes statistical significance vs. THP+/+ total kidney, whereas * denotes significance compared to THP-/- total kidney ($p<0.05$).
Figure 4B:
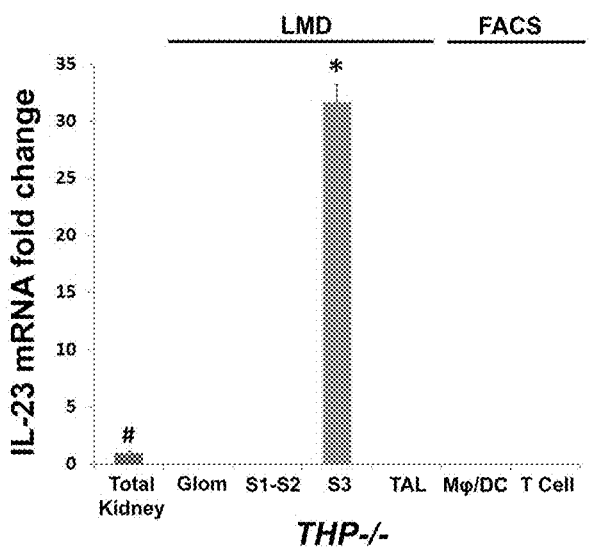

THP Regulates Neutrophil Infiltration and IL-23 Signaling in the Kidney Following AKI Neutrophil infiltration, which occurs in the early stages of AKI, is detrimental if it continues uninhibited. As illustrated by FIG. 3, AKI is associated with persistent neutrophil infiltration in THP−/− mice. It is now shown and described herein that THP deficiency results in increased IL-23 expression specifically in the S3 tubular epithelium of S3 segments, and not immune cells. For example, as indicated in FIG. 4B, IL-23 mRNA is specifically expressed in S3 segments from THP−/− kidneys. THP deficiency and subsequent increases in IL-23 in S3 tubular cells following AKI or in THP−/− kidneys resulted in initiation of pro-inflammatory signaling to produce and attract neutrophils.

Treatment of human proximal tubular cells (HK-2) with monomeric THP directly decreased IL-23 expression by these cells. In addition, oxidative insult using $H_2O_2$, but not LPS, stimulated IL-23 mRNA expression in these cells. These data show that oxidative stress, but not classical endotoxin signaling, is needed for IL-23 induction in epithelial cells.

THP Regulates IL-23 Expression in S3 Segments by Inhibiting the Rac-1-NOX2 Signaling Pathway of Oxidative Stress THP was observed to inhibit Rac-1/NOX2 oxidative stress in S3 segments. Inhibition of the Rac-1/NOX2 signaling pathway in turn regulates the production of IL-23 and activation of the IL-23/IL-17 pro-inflammatory axis.

Figures 5A, 5B, 5C:
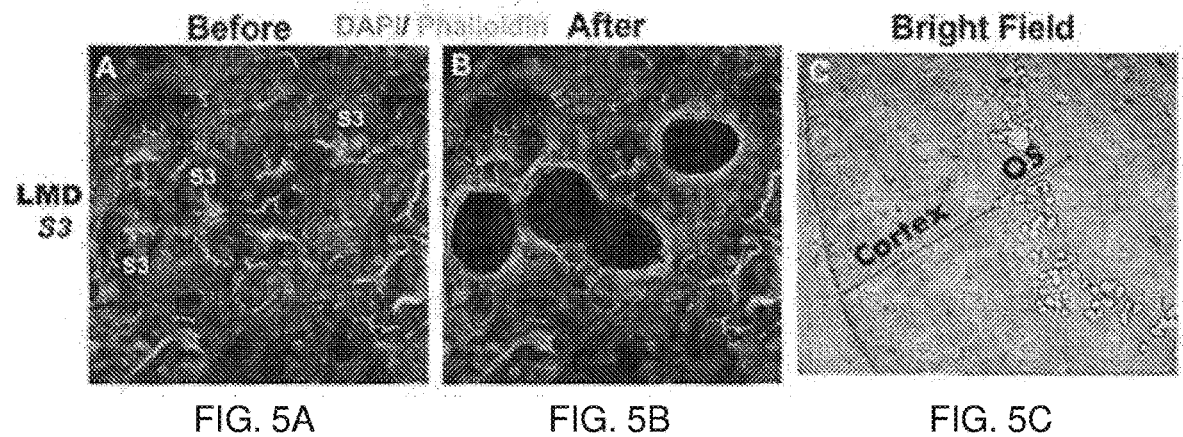
FIGS. 5A-5C are photographs of S3 proximal segments from THP-/- and THP+/+ kidneys following immunofluorescence laser micro-dissection (IF-LMD).
Figure 5D:
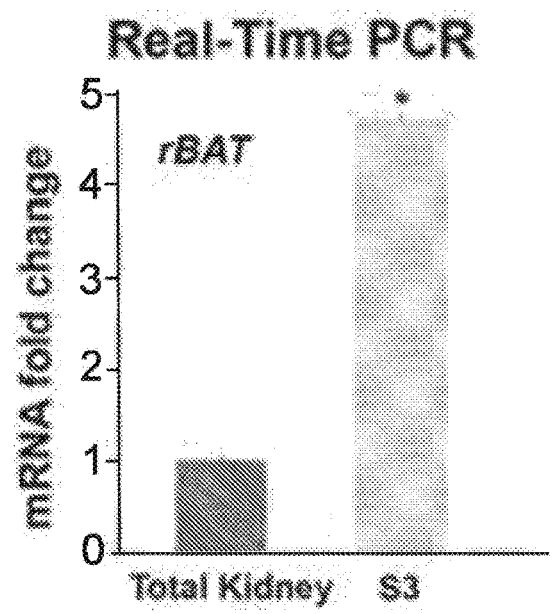
FIG. 5D is a bar graph representing elevated expression of marker protein rBAT in S3 proximal segments relative to total kidney.
Figures 5E, 5F, 5G:
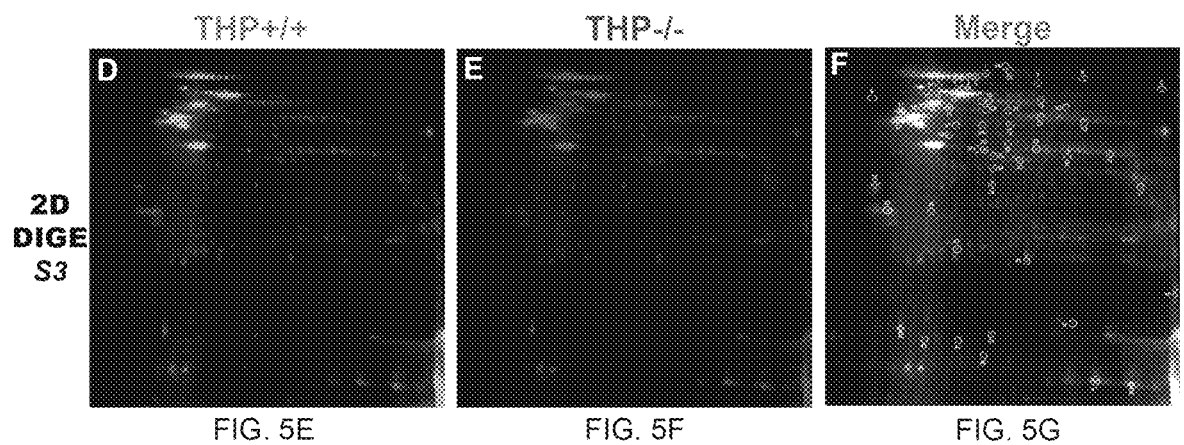
FIGS. 5E-5G are photographs of 2D-Difference gel electrophoresis (DIGE) on protein extracts from S3 segments from THP-/- and THP+/+ kidneys.
Figure 5H:
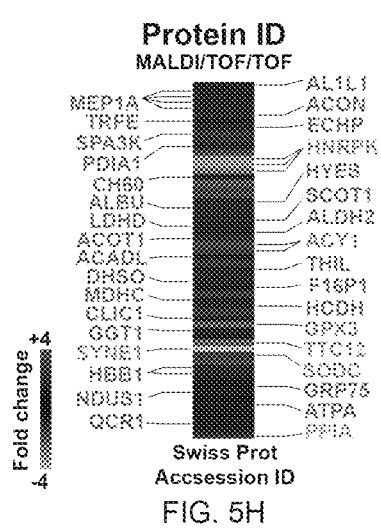
FIG. 5H indicates differentially regulated spots (>1.5 standard deviation fold change).
Figure 6A:
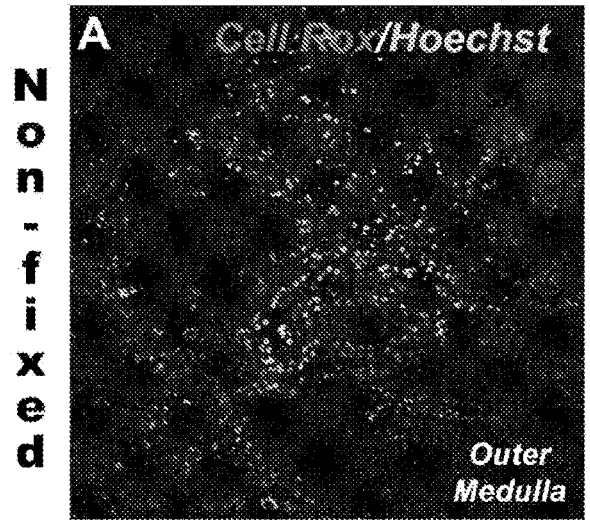
FIGS. 6A-6D are photographs representing oxidative stress in S3 segments in vivo. Uninjured THP+/+ and THP-/- mice were injected with IP Hoechst (blue nuclei) and CellRox (red). Kidneys were harvested 2 hours later and immediately section without fixation for detection of CellRox (FIGS. 6A and 6B). Another set of kidneys were fixed with 4% PFA, sectioned, and imaged a few days later after staining with Phalloidin (green.
Figure 6B:
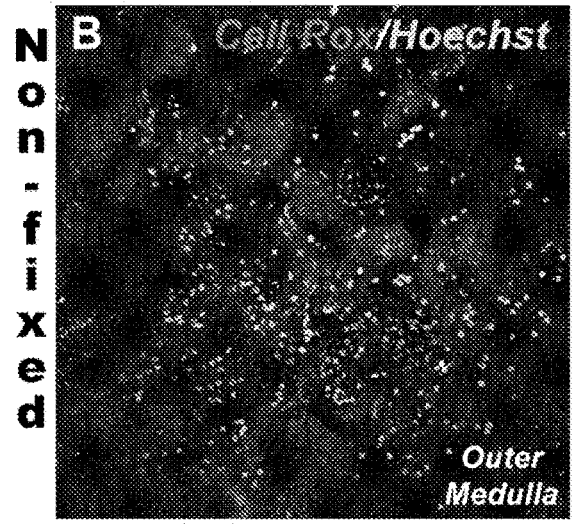
Figure 6C:
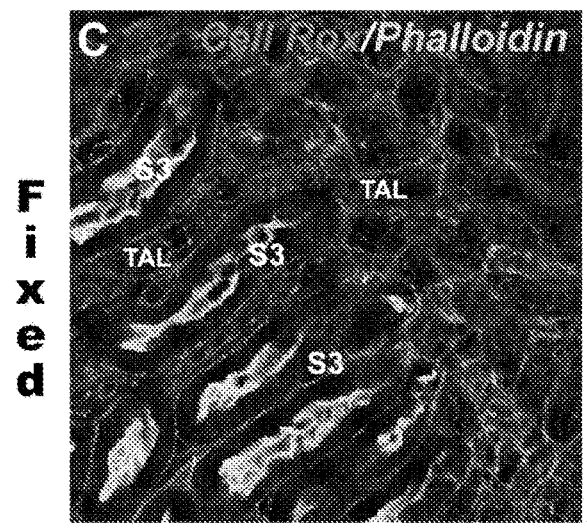
Figure 6D:
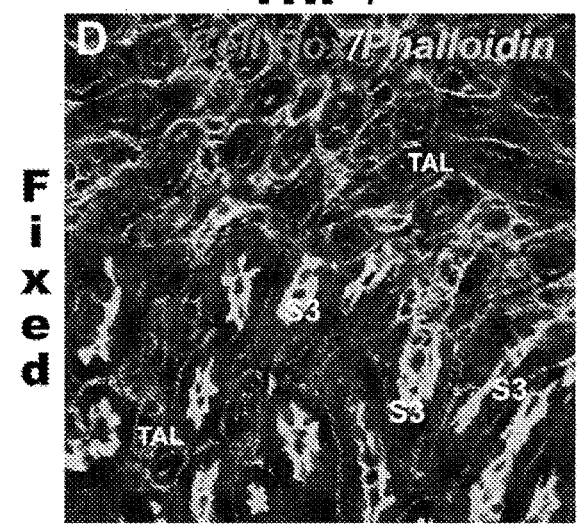

Immuno-fluorescence laser micro-dissection (IF-LMD) of S3 segments from uninjured THP−/− and THP+/+ kidney sections was performed. 2-Dimensional difference gel electrophoresis (2D-DIGE) was then used to identify pathways modulated by THP in vivo. FIGS. 5A-5G indicate isolation of S3 segments from THP−/− and THP+/+ kidneys (FIGS. 5A-5D), and results from 2D-DIGE (FIGS. 5E-5G) from the two strains of mice. Differentially expressed proteins were identified by mass spectrometry-MALDI/TOF/TOF (FIG. 5H).

Proteins involved in the quenching of oxidative stress, such as Superoxide dismutase-1 (SOD1) and Glutathione peroxidase-3 (GPX3), were significantly downregulated in THP−/− S3 segments. Bioinformatics analysis using Ingenuity showed that the free radical scavenging network was the most significantly affected, having the highest score of clustering. This data shows dysregulation of redox signaling in the S3 segments of THP−/− kidneys.

A fluorescent marker was then used as a marker of oxidative stress in vivo (FIGS. 6A-D). An increase in reactive oxygen species (ROS) generation was observed in the outer medulla of THP−/− compared to THP+/+ kidneys in the absence of injury. After fixing CellRox, S3 segments were identified as the site of increased ROS. Locating ROS in S3 segments was facilitated by brush border staining with phalloidin.

Figure 7:
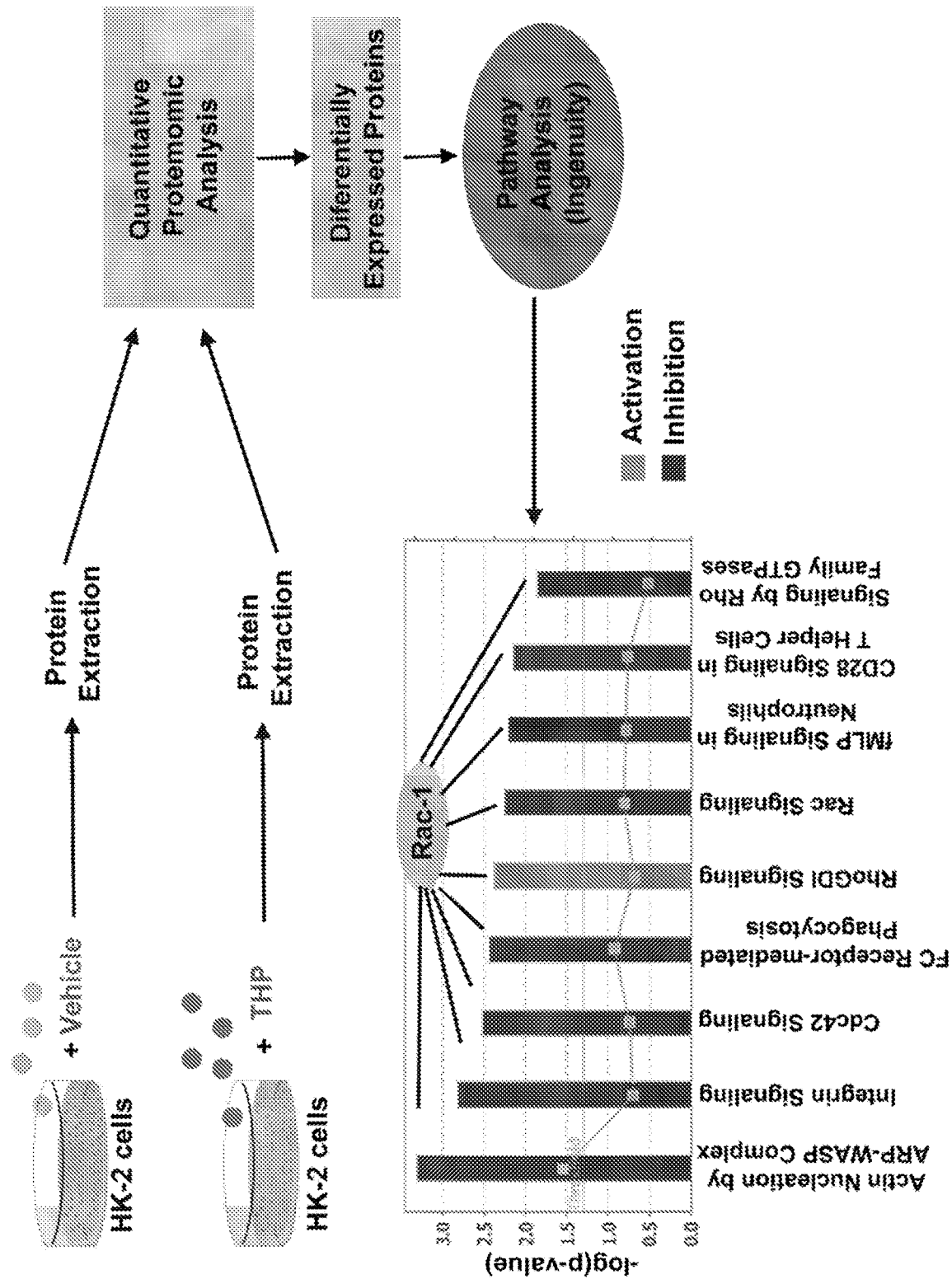
FIG. 7 illustrates label-free proteomic analysis of HK-2 cells treated with THP. Triplicate groups of HK-2 cells were treated with monomeric THP (1 µg/ml) or vehicle. Protein extraction was done followed by quantitative label-free proteomics. Differentially expressed proteins were identified, and canonical pathway analysis was performed using Ingenuity. Only significant pathways with Z score>2 or <−2 are represented, along with their predicted activation state.
Figure 8:
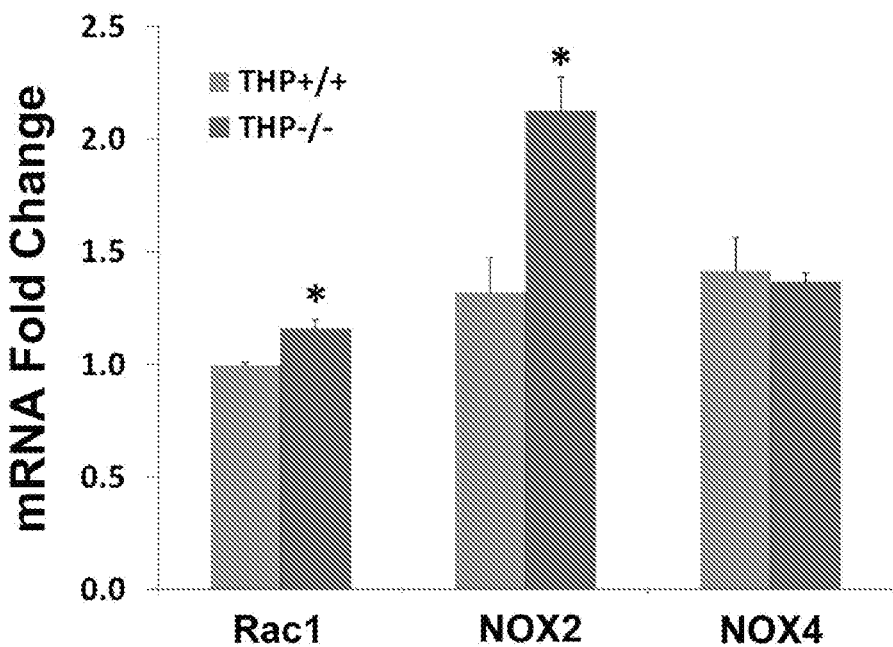
FIG. 8 is a bar graph indicating involvement of THP and Rac-1/Nox signaling pathway in oxidative stress. Bars represent real-time PCR measurements of Rac-1, Nox2, and Nox4 in total kidneys from THP+/+ and THP-/- mice. Rac1 and Nox2, but not Nox4, were significantly increased in THP-/- kidneys (n=5/group).

Human proximal tubular cells (HK-2) were then incubated with monomeric THP in culture. Label-free proteomic analysis of the HK-2 cells revealed that incubation of these cells with monomeric THP for 6 hours caused significant changes in the HK-2 proteome (FIG. 7). Monomeric THP inhibited multiple pathways that converge on Rac1 signaling (FIG. 7), as well as inhibited expression of Rac1 itself (FIG. 8).

Figures 9A, 9B:
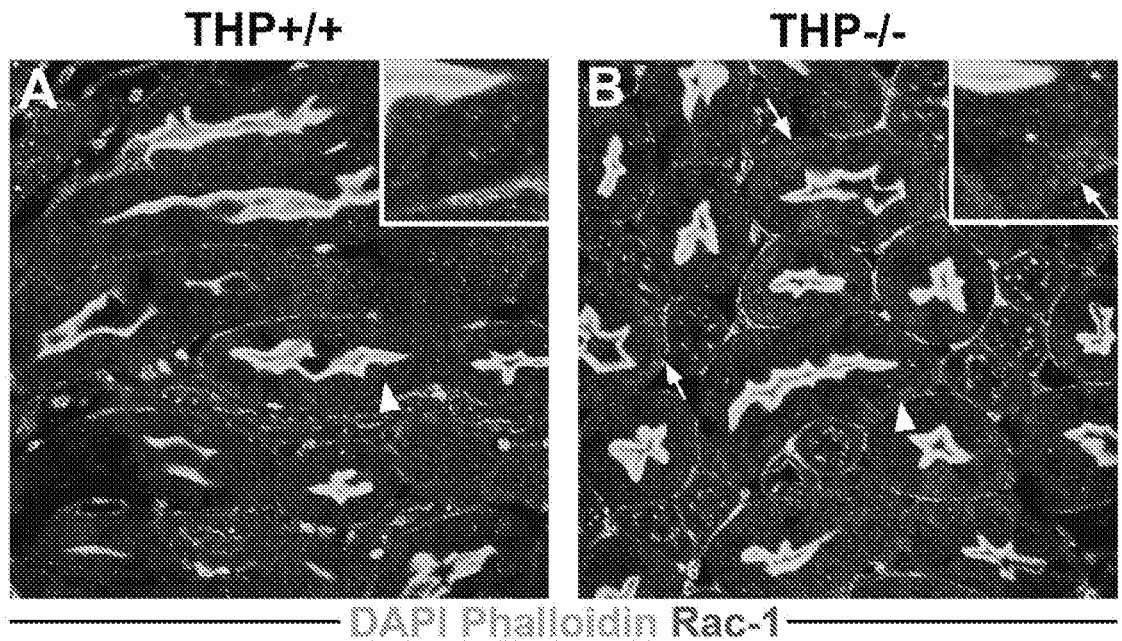
FIGS. 9A-9B are photographs of immunofluorescence confocal microscopy indicating shifting of Rac-1 (red) in THP-/- mice to the basolateral domain of S3 segments (FIG. 9B) compared to a cytoplasmic localization in THP+/+ (FIG. 9A). Insets represent a higher magnification (arrow points to basolateral Rac-1). Rac-1 shift is a surrogate for its activation.
Figure 9C:
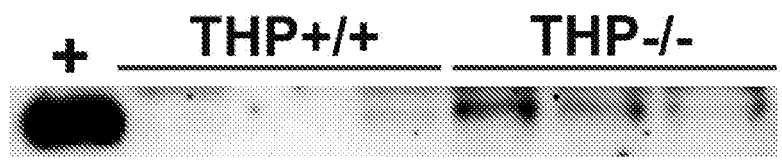
FIG. 9C is a photograph of a blot indicating results of a Rac-1 activation assay in total kidney lysates from THP+/+ and THP-/- kidneys, confirming increased Rac-1 activation with THP deficiency.

Rac1 signaling plays an important role in regulation of oxidative stress by activating NADPH oxidase (NOX). NOX activation is involved in the generation of ROS through the production of superoxides. By regulating Rac1/NOX signaling, THP regulates ROS generation, and in turn, inflammation. There are several NOX isoforms. The kidney expresses predominantly NOX1, NOX2, and NOX4. Using real-time PCR, expression of Rac1 and NOX2, but not NOX4, was determined to be higher in THP−/− compared to THP+/+ kidneys (FIG. 8). NOX1 could not be detected in kidneys from either mouse strain. Immunofluorescence confocal microscopy showed that THP deficiency results in Rac1 activation in S3 epithelium (FIGS. 9A-9B). Rac1 in THP−/− mice shifted to the basolateral domain of S3 segments, compared to a cytoplasmic localization in THP+/+. The Rac-1 shift indicates activation. Activation of Rac1 in the THP deficient −/− kidney was confirmed by Rac1 activation assay (FIG. 9C). These data show that THP regulates Rac1/NOX signaling.

The data described show that monomeric THP inhibits Rac1/NOX2 oxidative stress in S3 segments, which in turn regulates the production of IL-23 and activation of the IL-23/IL-17 axis. Through these pathways, monomeric THP regulates oxidative stress in S3 segments, inhibiting an inflammatory signaling pathway leading to neutrophil infiltration after, for example, AKI.

THP Deficiency Causes Macrophage Depletion in the Kidney

Figure 10:
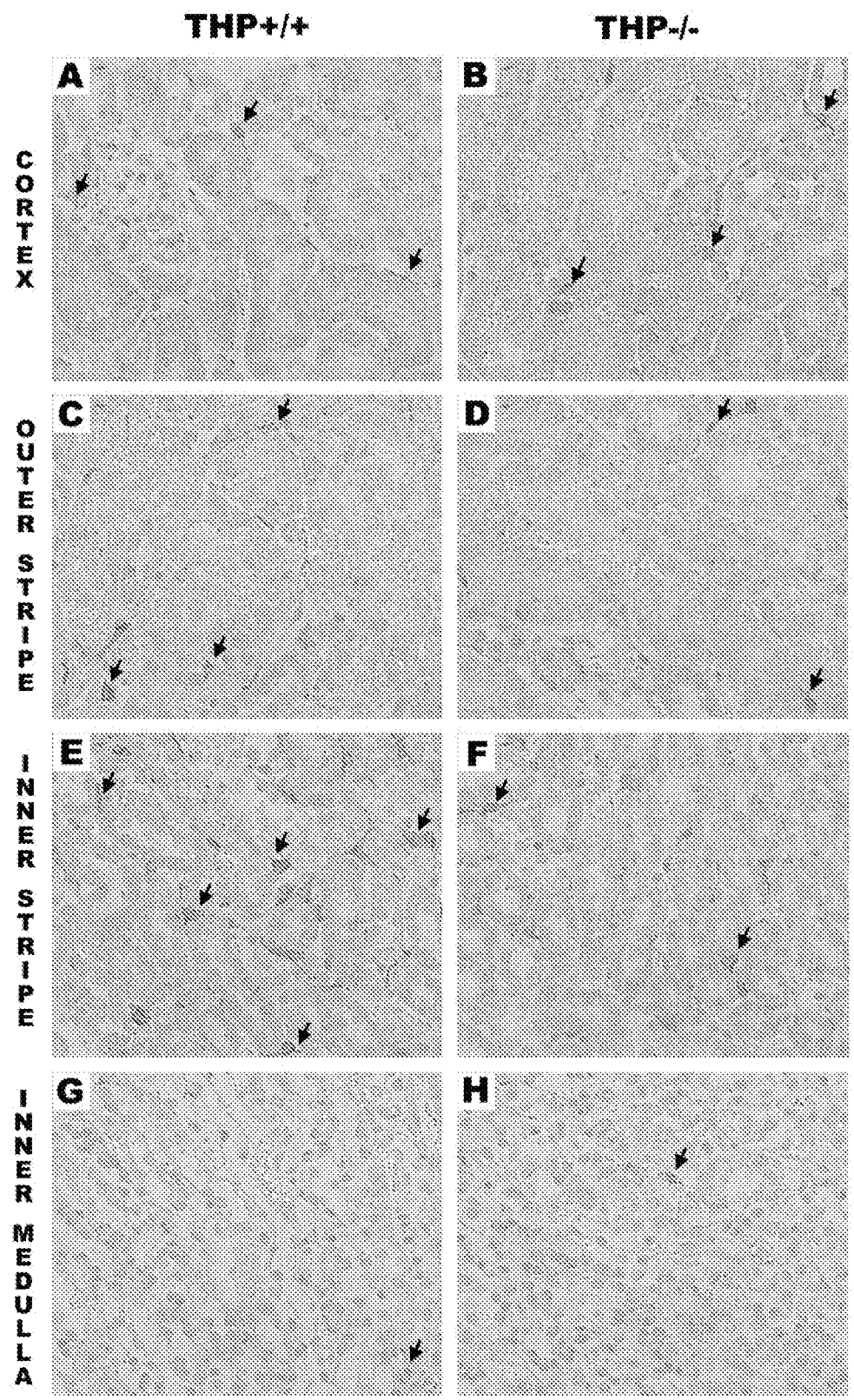
FIG. 10 are photographs (panels A-H) indicating a reduced number of F4-80+ macrophages in THP-/- kidney relative to THP+/+ kidney.
Figure 11:
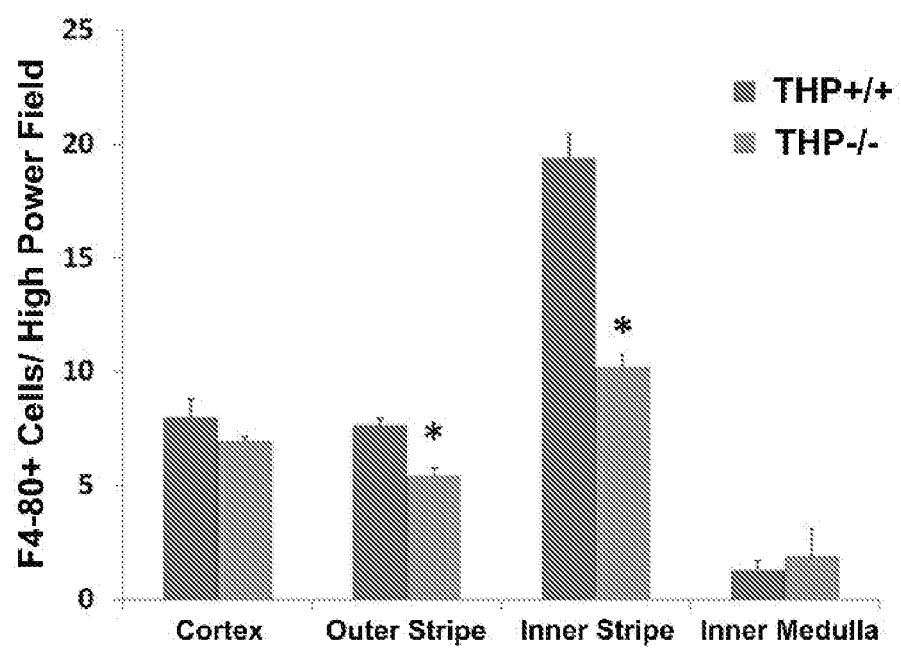
FIG. 11 is a bar graph indicating the reduced number of F4-80+ macrophages in THP-/- kidney relative to THP+/+ kidney, as depicted in FIG. 10.

Immunohistochemistry analysis of kidneys from THP−/− and THP+/+ mice revealed a significant decrease in F4-80+ macrophage number in THP−/− kidneys (FIG. 10 and FIG. 11). Reduction in macrophage number was not observed in other organs tested, including liver and spleen.

Figure 12:
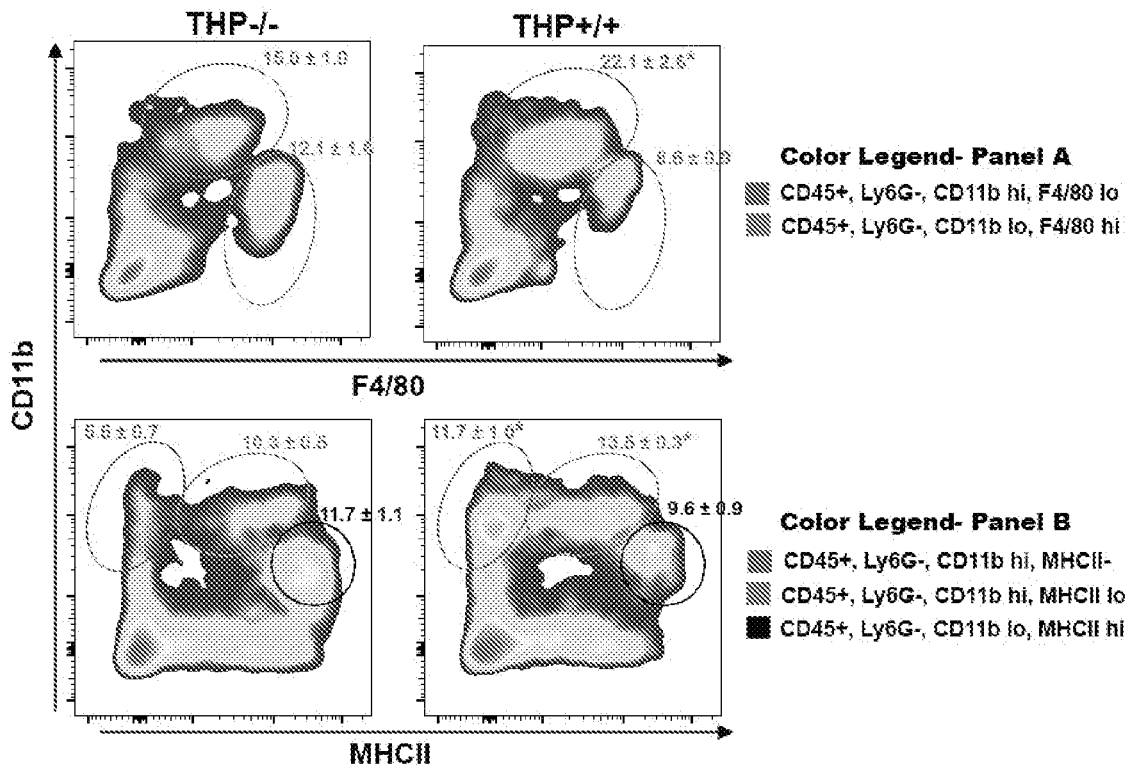
FIG. 12 depicts flow cytometry results, which indicate that THP deficiency causes macrophage depletion in the kidney. Plots represent flow cytometry results of kidneys from THP+/+ and THP-/- mice (n=5 per group). The numbers are percentages of cells out of total number of CD45+ cells. * denotes statistical significance between the two strains ($p<0.05$). There is reduction in macrophage numbers shown both in the upper two panels and lower two panels using different markers, but not in dendritic cells (defined as CD11b lo, MHCII hi and F4/80 hi).

Macrophage depletion resulting from THP deficiency was confirmed by flow cytometry (FIG. 12). The flow cytometry experiments utilized the markers CD11b, MHCII and F4/80, and showed a significant reduction in number of macrophage from THP+/+ kidney to THP−/− kidney. No reduction in dendritic cell numbers was observed.

Figure 13:
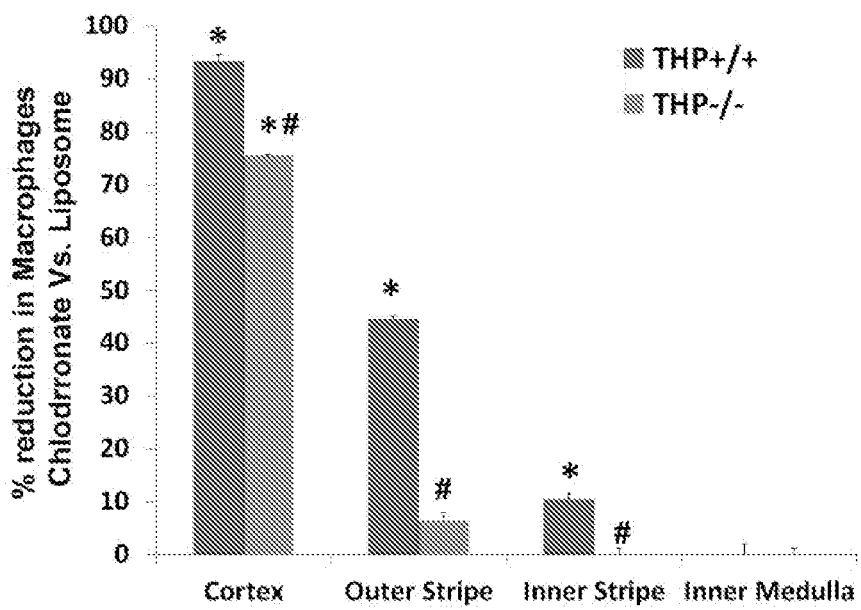
FIG. 13 is a bar graph indicating that THP deficiency reduces the phagocytic activity of macrophages in vivo. Bars are mean+/−standard error of percentage reduction of F4/80+ macrophages in kidney sections from THP+/+ and THP-/- mice 48 hours after treatment with liposomal chlodronate or empty liposomes. The killing of macrophages by chlodronate requires active phagocytosis of liposomal chlodronate by macrophages. THP+/+ mice have significant reduction in macrophages in most areas of the kidneys. THP−/− mice have only a reduction in macrophages in the cortex but not other areas. * denotes significant reduction vs. liposome controls. # denotes statistical significance between strains.

THP deficiency was further shown to reduce the phagocytic activity of macrophages in vivo (FIG. 13). FIG. 13 represents the percentage reduction of F4/80+ macrophages in kidney sections from THP−/− and THP+/+ mice 48 hours after treatment with liposomal chlodronate (a macrophage toxin) or empty liposomes. The killing of macrophages by chlodronate requires active phagocytosis of liposomal chlodronate by macrophages. THP+/+ mice showed a significant reduction in macrophages in most areas of the kidneys, indicating active phagocytosis of liposomal chlodronate by the macrophages. THP−/− mice only showed a significant reduction in macrophages in the cortex, but not in other areas. These data show that the in vivo phagocytic activity of macrophages is impaired by THP deficiency.

Example 5—Use of THP to Modulate an Immune Response

As discussed in Example 3, monomeric THP affects several immune responses, including inflammatory signaling, macrophage activation, and macrophage number.

In methods for modulating an immune response in a subject, a therapeutically effective amount of a pharmaceutical composition including about 0.2 mg/kg to about 10.0 mg/kg monomeric THP or a biologically active truncated THP is administered to a subject to modulate an immune response in the subject, such as inhibiting inflammatory signaling and increasing the number and activation state of macrophage. Effects can be systemic or localized to the kidney.

Modulation of the immune response in the subject can be beneficial where the subject suffers from, for example, sepsis, transplant rejection, and the like.

Example 6—Use of THP as an Adjuvant

Polypeptides described herein can be used to boost or improve an immune response in a subject to, for example, an immunogenic composition such as a vaccine composition. This is due to their ability to inhibit inflammatory signaling and cause proliferation and activation of renal macrophage.

In methods for boosting or improving an immune response in a subject to an immunogenic composition, a therapeutically effective amount of a pharmaceutical composition including from about 0.2 mg/kg to about 10.0 mg/kg monomeric THP or a biologically active truncated THP can be administered to a subject. The pharmaceutical composition can be the vaccine itself, or a separate pharmaceutical composition. The monomeric THP or biologically active truncated THP can stimulate the immune system of the subject, potentiating the immune response to the antigen of the vaccine.

All of the compositions and methods disclosed and claimed herein can be made and executed without undue experimentation in light of the present disclosure. While the compositions and methods have been described in terms of particular embodiments, it is apparent to those of skill in the art that variations may be applied to the compositions and methods and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A purified or isolated polypeptide consisting of an amino acid sequence at least 95% identical to an amino acid sequence chosen from SEQ ID NO: 2, SEQ ID NO: 3, SEQ ID NO: 4, SEQ ID NO: 5, SEQ ID NO:6, and SEQ ID NO: 7.

2. The purified or isolated polypeptide of claim 1, wherein the purified or isolated polypeptide consists of an amino acid sequence chosen from SEQ ID NO: 2, SEQ ID NO: 3, SEQ ID NO: 4, SEQ ID NO: 5, SEQ ID NO:6, and SEQ ID NO: 7.

3. A pharmaceutical composition comprising the purified or isolated polypeptide of claim 1 and a pharmaceutically acceptable carrier.

4. The pharmaceutical composition of claim 3, further comprising a purified or isolated polypeptide comprising an amino acid sequence at least 85% identical to an amino acid sequence according to SEQ ID NO: 1.

5. A method for treating at least one renal disease, disorder, or condition in a subject, the method comprising administering to the subject an effective amount of the purified or isolated polypeptide of claim 1, or both the purified or isolated polypeptide of claim 1 and a purified or isolated polypeptide comprising an amino acid sequence at least 85% identical to an amino acid sequence according to SEQ ID NO: 1, wherein the at least one renal disease, disorder, of condition comprises at least one of: acute kidney injury, sepsis, transplant rejection, and chronic kidney disease.

6. The method according to claim 5, wherein the polypeptide or the pharmaceutical composition is administered orally, intravenously, intraperitoneally, intramuscularly, or subcutaneously.

7. The method according to claim 5, wherein the effective amount is between about 0.2 mg/kg and about 10.0 mg/kg of the polypeptide.

8. The method according to claim 5, wherein the effective amount is between about 0.2 mg/kg and about 3.0 mg/kg of the polypeptide.

9. A method for treating at least one renal disease, disorder, or condition in a subject, the method comprising administering to the subject an effective amount of the pharmaceutical composition of claim 3, or a pharmaceutical composition of claim 3 further comprising a polypeptide comprising an amino acid sequence at least 85% identical to an amino acid sequence according to SEQ ID NO: 1, wherein the at least one renal disease, disorder, of condition comprises at least one of: acute kidney injury, sepsis, transplant rejection, and chronic kidney disease.

10. The method according to claim 9, wherein the polypeptide or the pharmaceutical composition is administered orally, intravenously, intraperitoneally, intramuscularly, or subcutaneously.

11. The method according to claim 9, wherein the effective amount is between about 0.2 mg/kg and about 10.0 mg/kg of the polypeptide.

12. The method according to claim 9, wherein the effective amount is between about 0.2 mg/kg and about 3.0 mg/kg of the polypeptide.

13. An immunogenic composition comprising at least one immunogenic agent and the purified or isolated polypeptide of claim 1.

14. A method for enhancing an immune response to an immunogenic composition in a subject, the method comprising administering to the subject an effective amount of the purified or isolated polypeptide of claim 1.

15. A purified or isolated polypeptide consisting of an amino acid sequence at least 95% identical to SEQ ID NO: 7.

16. A pharmaceutical composition comprising the purified or isolated polypeptide of claim 15 and a pharmaceutically acceptable carrier.

17. A method for treating at least one renal disease, disorder, or condition in a subject, the method comprising administering to the subject an effective amount of the purified or isolated polypeptide of claim 15.

18. The purified or isolated polypeptide of claim 1, further comprising a polypeptide half-life increasing compound or a peptide purification tag linked to the isolated polypeptide.

19. The purified or isolated polypeptide of claim 15, further comprising polypeptide half-life increasing compound or a peptide purification tag linked to the isolated polypeptide.

* * * * *

SEQUENCE LISTING

```
<160> NUMBER OF SEQ ID NOS: 7

<210> SEQ ID NO 1
<211> LENGTH: 640
<212> TYPE: PRT
<213> ORGANISM: Homo sapiens

<400> SEQUENCE: 1

Met Gly Gln Pro Ser Leu Thr Trp Met Leu Met Val Val Val Ala Ser
1               5                   10                  15

Trp Phe Ile Thr Thr Ala Ala Thr Asp Thr Ser Glu Ala Arg Trp Cys
            20                  25                  30

Ser Glu Cys His Ser Asn Ala Thr Cys Thr Glu Asp Glu Ala Val Thr
        35                  40                  45

Thr Cys Thr Cys Gln Glu Gly Phe Thr Gly Asp Gly Leu Thr Cys Val
    50                  55                  60

Asp Leu Asp Glu Cys Ala Ile Pro Gly Ala His Asn Cys Ser Ala Asn
65                  70                  75                  80

Ser Ser Cys Val Asn Thr Pro Gly Ser Phe Ser Cys Val Cys Pro Glu
                85                  90                  95

Gly Phe Arg Leu Ser Pro Gly Leu Gly Cys Thr Asp Val Asp Glu Cys
            100                 105                 110

Ala Glu Pro Gly Leu Ser His Cys His Ala Leu Ala Thr Cys Val Asn
            115                 120                 125

Val Val Gly Ser Tyr Leu Cys Val Cys Pro Ala Gly Tyr Arg Gly Asp
    130                 135                 140

Gly Trp His Cys Glu Cys Ser Pro Gly Ser Cys Gly Pro Gly Leu Asp
145                 150                 155                 160

Cys Val Pro Glu Gly Asp Ala Leu Val Cys Ala Asp Pro Cys Gln Ala
                165                 170                 175

His Arg Thr Leu Asp Glu Tyr Trp Arg Ser Thr Glu Tyr Gly Glu Gly
            180                 185                 190

Tyr Ala Cys Asp Thr Asp Leu Arg Gly Trp Tyr Arg Phe Val Gly Gln
            195                 200                 205

Gly Gly Ala Arg Met Ala Glu Thr Cys Val Pro Val Leu Arg Cys Asn
    210                 215                 220
```

-continued

Thr Ala Ala Pro Met Trp Leu Asn Gly Thr His Pro Ser Ser Asp Glu
225                 230                 235                 240

Gly Ile Val Ser Arg Lys Ala Cys Ala His Trp Ser Gly His Cys Cys
            245                 250                 255

Leu Trp Asp Ala Ser Val Gln Val Lys Ala Cys Ala Gly Gly Tyr Tyr
            260                 265                 270

Val Tyr Asn Leu Thr Ala Pro Pro Glu Cys His Leu Ala Tyr Cys Thr
            275                 280                 285

Asp Pro Ser Ser Val Glu Gly Thr Cys Glu Cys Ser Ile Asp Glu
    290                 295                 300

Asp Cys Lys Ser Asn Asn Gly Arg Trp His Cys Gln Cys Lys Gln Asp
305                 310                 315                 320

Phe Asn Ile Thr Asp Ile Ser Leu Leu Glu His Arg Leu Glu Cys Gly
            325                 330                 335

Ala Asn Asp Met Lys Val Ser Leu Gly Lys Cys Gln Leu Lys Ser Leu
            340                 345                 350

Gly Phe Asp Lys Val Phe Met Tyr Leu Ser Asp Ser Arg Cys Ser Gly
    355                 360                 365

Phe Asn Asp Arg Asp Asn Arg Asp Trp Val Ser Val Val Thr Pro Ala
370                 375                 380

Arg Asp Gly Pro Cys Gly Thr Val Leu Thr Arg Asn Glu Thr His Ala
385                 390                 395                 400

Thr Tyr Ser Asn Thr Leu Tyr Leu Ala Asp Glu Ile Ile Arg Asp
            405                 410                 415

Leu Asn Ile Lys Ile Asn Phe Ala Cys Ser Tyr Pro Leu Asp Met Lys
            420                 425                 430

Val Ser Leu Lys Thr Ala Leu Gln Pro Met Val Ser Ala Leu Asn Ile
        435                 440                 445

Arg Val Gly Gly Thr Gly Met Phe Thr Val Arg Met Ala Leu Phe Gln
    450                 455                 460

Thr Pro Ser Tyr Thr Gln Pro Tyr Gln Gly Ser Ser Val Thr Leu Ser
465                 470                 475                 480

Thr Glu Ala Phe Leu Tyr Val Gly Thr Met Leu Asp Gly Gly Asp Leu
            485                 490                 495

Ser Arg Phe Ala Leu Leu Met Thr Asn Cys Tyr Ala Thr Pro Ser Ser
        500                 505                 510

Asn Ala Thr Asp Pro Leu Lys Tyr Phe Ile Ile Gln Asp Arg Cys Pro
        515                 520                 525

His Thr Arg Asp Ser Thr Ile Gln Val Val Glu Asn Gly Glu Ser Ser
    530                 535                 540

Gln Gly Arg Phe Ser Val Gln Met Phe Arg Phe Ala Gly Asn Tyr Asp
545                 550                 555                 560

Leu Val Tyr Leu His Cys Glu Val Tyr Leu Cys Asp Thr Met Asn Glu
            565                 570                 575

Lys Cys Lys Pro Thr Cys Ser Gly Thr Arg Phe Arg Ser Gly Ser Val
        580                 585                 590

Ile Asp Gln Ser Arg Val Leu Asn Leu Gly Pro Ile Thr Arg Lys Gly
    595                 600                 605

Val Gln Ala Thr Val Ser Arg Ala Phe Ser Ser Leu Gly Leu Leu Lys
    610                 615                 620

Val Trp Leu Pro Leu Leu Leu Ser Ala Thr Leu Thr Leu Thr Phe Gln
625                 630                 635                 640

```
<210> SEQ ID NO 2
<211> LENGTH: 313
<212> TYPE: PRT
<213> ORGANISM: Artificial Sequence
<220> FEATURE:
<223> OTHER INFORMATION: Synthetic

<400> SEQUENCE: 2

Asp Thr Ser Glu Ala Arg Trp Cys Ser Glu Cys His Ser Asn Ala Thr
1               5                   10                  15

Cys Thr Glu Asp Glu Ala Val Thr Thr Cys Thr Cys Gln Glu Gly Phe
            20                  25                  30

Thr Gly Asp Gly Leu Thr Cys Val Asp Leu Asp Glu Cys Ala Ile Pro
        35                  40                  45

Gly Ala His Asn Cys Ser Ala Asn Ser Ser Cys Val Asn Thr Pro Gly
    50                  55                  60

Ser Phe Ser Cys Val Cys Pro Glu Gly Phe Arg Leu Ser Pro Gly Leu
65                  70                  75                  80

Gly Cys Thr Asp Val Asp Glu Cys Ala Glu Pro Gly Leu Ser His Cys
                85                  90                  95

His Ala Leu Ala Thr Cys Val Asn Val Val Gly Ser Tyr Leu Cys Val
            100                 105                 110

Cys Pro Ala Gly Tyr Arg Gly Asp Gly Trp His Cys Glu Cys Ser Pro
        115                 120                 125

Gly Ser Cys Gly Pro Gly Leu Asp Cys Val Pro Glu Gly Asp Ala Leu
    130                 135                 140

Val Cys Ala Asp Pro Cys Gln Ala His Arg Thr Leu Asp Glu Tyr Trp
145                 150                 155                 160

Arg Ser Thr Glu Tyr Gly Glu Gly Tyr Ala Cys Asp Thr Asp Leu Arg
                165                 170                 175

Gly Trp Tyr Arg Phe Val Gly Gln Gly Gly Ala Arg Met Ala Glu Thr
            180                 185                 190

Cys Val Pro Val Leu Arg Cys Asn Thr Ala Ala Pro Met Trp Leu Asn
        195                 200                 205

Gly Thr His Pro Ser Ser Asp Glu Gly Ile Val Ser Arg Lys Ala Cys
    210                 215                 220

Ala His Trp Ser Gly His Cys Cys Leu Trp Asp Ala Ser Val Gln Val
225                 230                 235                 240

Lys Ala Cys Ala Gly Gly Tyr Tyr Val Tyr Asn Leu Thr Ala Pro Pro
                245                 250                 255

Glu Cys His Leu Ala Tyr Cys Thr Asp Pro Ser Ser Val Glu Gly Thr
            260                 265                 270

Cys Glu Glu Cys Ser Ile Asp Glu Asp Cys Lys Ser Asn Asn Gly Arg
        275                 280                 285

Trp His Cys Gln Cys Lys Gln Asp Phe Asn Ile Thr Asp Ile Ser Leu
    290                 295                 300

Leu Glu His Arg Leu Glu Cys Gly Ala
305                 310

<210> SEQ ID NO 3
<211> LENGTH: 265
<212> TYPE: PRT
<213> ORGANISM: Artificial Sequence
<220> FEATURE:
<223> OTHER INFORMATION: Synthetic

<400> SEQUENCE: 3
```

Asp Thr Ser Glu Ala Arg Trp Cys Ser Glu Cys His Ser Asn Ala Thr
1               5                   10                  15

Cys Thr Glu Asp Glu Ala Val Thr Thr Cys Thr Cys Gln Gly Phe
            20                  25                  30

Thr Gly Asp Gly Leu Thr Cys Val Asp Leu Asp Glu Cys Ala Ile Pro
        35                  40                  45

Gly Ala His Asn Cys Ser Ala Asn Ser Ser Cys Val Asn Thr Pro Gly
    50                  55                  60

Ser Phe Ser Cys Val Cys Pro Glu Gly Phe Arg Leu Ser Pro Gly Leu
65              70                  75                  80

Gly Cys Thr Asp Val Asp Glu Cys Ala Glu Pro Gly Leu Ser His Cys
            85                  90                  95

His Ala Leu Ala Thr Cys Val Asn Val Val Gly Ser Tyr Leu Cys Val
                100                 105                 110

Cys Pro Ala Gly Tyr Arg Gly Asp Gly Trp His Cys Glu Cys Ser Pro
            115                 120                 125

Gly Ser Cys Gly Pro Gly Leu Asp Cys Val Pro Glu Gly Asp Ala Leu
        130                 135                 140

Val Cys Ala Asp Pro Cys Gln Ala His Arg Thr Leu Asp Glu Tyr Trp
145                 150                 155                 160

Arg Ser Thr Glu Tyr Gly Glu Gly Tyr Ala Cys Asp Thr Asp Leu Arg
                165                 170                 175

Gly Trp Tyr Arg Phe Val Gly Gln Gly Gly Ala Arg Met Ala Glu Thr
            180                 185                 190

Cys Val Pro Val Leu Arg Cys Asn Thr Ala Ala Pro Met Trp Leu Asn
            195                 200                 205

Gly Thr His Pro Ser Ser Asp Glu Gly Ile Val Ser Arg Lys Ala Cys
    210                 215                 220

Ala His Trp Ser Gly His Cys Cys Leu Trp Asp Ala Ser Val Gln Val
225                 230                 235                 240

Lys Ala Cys Ala Gly Gly Tyr Tyr Val Tyr Asn Leu Thr Ala Pro Pro
            245                 250                 255

Glu Cys His Leu Ala Tyr Cys Thr Asp
        260                 265

<210> SEQ ID NO 4
<211> LENGTH: 125
<212> TYPE: PRT
<213> ORGANISM: Artificial Sequence
<220> FEATURE:
<223> OTHER INFORMATION: Synthetic

<400> SEQUENCE: 4

Asp Thr Ser Glu Ala Arg Trp Cys Ser Glu Cys His Ser Asn Ala Thr
1               5                   10                  15

Cys Thr Glu Asp Glu Ala Val Thr Thr Cys Thr Cys Gln Gly Phe
            20                  25                  30

Thr Gly Asp Gly Leu Thr Cys Val Asp Leu Asp Glu Cys Ala Ile Pro
        35                  40                  45

Gly Ala His Asn Cys Ser Ala Asn Ser Ser Cys Val Asn Thr Pro Gly
    50                  55                  60

Ser Phe Ser Cys Val Cys Pro Glu Gly Phe Arg Leu Ser Pro Gly Leu
65              70                  75                  80

Gly Cys Thr Asp Val Asp Glu Cys Ala Glu Pro Gly Leu Ser His Cys
            85                  90                  95

His Ala Leu Ala Thr Cys Val Asn Val Val Gly Ser Tyr Leu Cys Val
            100                 105                 110

Cys Pro Ala Gly Tyr Arg Gly Asp Gly Trp His Cys Glu
        115                 120                 125

<210> SEQ ID NO 5
<211> LENGTH: 590
<212> TYPE: PRT
<213> ORGANISM: Homo sapiens

<400> SEQUENCE: 5

Asp Thr Ser Glu Ala Arg Trp Cys Ser Glu Cys His Ser Asn Ala Thr
1               5                   10                  15

Cys Thr Glu Asp Glu Ala Val Thr Thr Cys Thr Cys Gln Glu Gly Phe
            20                  25                  30

Thr Gly Asp Gly Leu Thr Cys Val Asp Leu Asp Glu Cys Ala Ile Pro
        35                  40                  45

Gly Ala His Asn Cys Ser Ala Asn Ser Ser Cys Val Asn Thr Pro Gly
    50                  55                  60

Ser Phe Ser Cys Val Cys Pro Glu Gly Phe Arg Leu Ser Pro Gly Leu
65                  70                  75                  80

Gly Cys Thr Asp Val Asp Glu Cys Ala Glu Pro Gly Leu Ser His Cys
                85                  90                  95

His Ala Leu Ala Thr Cys Val Asn Val Val Gly Ser Tyr Leu Cys Val
            100                 105                 110

Cys Pro Ala Gly Tyr Arg Gly Asp Gly Trp His Cys Glu Cys Ser Pro
        115                 120                 125

Gly Ser Cys Gly Pro Gly Leu Asp Cys Val Pro Glu Gly Asp Ala Leu
    130                 135                 140

Val Cys Ala Asp Pro Cys Gln Ala His Arg Thr Leu Asp Glu Tyr Trp
145                 150                 155                 160

Arg Ser Thr Glu Tyr Gly Glu Gly Tyr Ala Cys Asp Thr Asp Leu Arg
                165                 170                 175

Gly Trp Tyr Arg Phe Val Gly Gln Gly Gly Ala Arg Met Ala Glu Thr
            180                 185                 190

Cys Val Pro Val Leu Arg Cys Asn Thr Ala Ala Pro Met Trp Leu Asn
        195                 200                 205

Gly Thr His Pro Ser Ser Asp Glu Gly Ile Val Ser Arg Lys Ala Cys
    210                 215                 220

Ala His Trp Ser Gly His Cys Cys Leu Trp Asp Ala Ser Val Gln Val
225                 230                 235                 240

Lys Ala Cys Ala Gly Gly Tyr Tyr Val Tyr Asn Leu Thr Ala Pro Pro
                245                 250                 255

Glu Cys His Leu Ala Tyr Cys Thr Asp Pro Ser Ser Val Glu Gly Thr
            260                 265                 270

Cys Glu Glu Cys Ser Ile Asp Glu Asp Cys Lys Ser Asn Asn Gly Arg
        275                 280                 285

Trp His Cys Gln Cys Lys Gln Asp Phe Asn Ile Thr Asp Ile Ser Leu
    290                 295                 300

Leu Glu His Arg Leu Glu Cys Gly Ala Asn Asp Met Lys Val Ser Leu
305                 310                 315                 320

Gly Lys Cys Gln Leu Lys Ser Leu Gly Phe Asp Lys Val Phe Met Tyr
                325                 330                 335

Leu Ser Asp Ser Arg Cys Ser Gly Phe Asn Asp Arg Asp Asn Arg Asp
            340                 345                 350

```
Trp Val Ser Val Val Thr Pro Ala Arg Asp Gly Pro Cys Gly Thr Val
        355                 360                 365

Leu Thr Arg Asn Glu Thr His Ala Thr Tyr Ser Asn Thr Leu Tyr Leu
    370                 375                 380

Ala Asp Glu Ile Ile Ile Arg Asp Leu Asn Ile Lys Ile Asn Phe Ala
385                 390                 395                 400

Cys Ser Tyr Pro Leu Asp Met Lys Val Ser Leu Lys Thr Ala Leu Gln
            405                 410                 415

Pro Met Val Ser Ala Leu Asn Ile Arg Val Gly Gly Thr Gly Met Phe
        420                 425                 430

Thr Val Arg Met Ala Leu Phe Gln Thr Pro Ser Tyr Thr Gln Pro Tyr
    435                 440                 445

Gln Gly Ser Ser Val Thr Leu Ser Thr Glu Ala Phe Leu Tyr Val Gly
        450                 455                 460

Thr Met Leu Asp Gly Gly Asp Leu Ser Arg Phe Ala Leu Leu Met Thr
465                 470                 475                 480

Asn Cys Tyr Ala Thr Pro Ser Ser Asn Ala Thr Asp Pro Leu Lys Tyr
            485                 490                 495

Phe Ile Ile Gln Asp Arg Cys Pro His Thr Arg Asp Ser Thr Ile Gln
        500                 505                 510

Val Val Glu Asn Gly Glu Ser Ser Gln Gly Arg Phe Ser Val Gln Met
    515                 520                 525

Phe Arg Phe Ala Gly Asn Tyr Asp Leu Val Tyr Leu His Cys Glu Val
    530                 535                 540

Tyr Leu Cys Asp Thr Met Asn Glu Lys Cys Lys Pro Thr Cys Ser Gly
545                 550                 555                 560

Thr Arg Phe Arg Ser Gly Ser Val Ile Asp Gln Ser Arg Val Leu Asn
            565                 570                 575

Leu Gly Pro Ile Thr Arg Lys Gly Val Gln Ala Thr Val Ser
            580                 585                 590

<210> SEQ ID NO 6
<211> LENGTH: 563
<212> TYPE: PRT
<213> ORGANISM: Homo sapiens

<400> SEQUENCE: 6

Asp Thr Ser Glu Ala Arg Trp Cys Ser Glu Cys His Ser Asn Ala Thr
1               5                   10                  15

Cys Thr Glu Asp Glu Ala Val Thr Thr Cys Thr Cys Gln Glu Gly Phe
            20                  25                  30

Thr Gly Asp Gly Leu Thr Cys Val Asp Leu Asp Glu Cys Ala Ile Pro
        35                  40                  45

Gly Ala His Asn Cys Ser Ala Asn Ser Ser Cys Val Asn Thr Pro Gly
    50                  55                  60

Ser Phe Ser Cys Val Cys Pro Glu Gly Phe Arg Leu Ser Pro Gly Leu
65                  70                  75                  80

Gly Cys Thr Asp Val Asp Glu Cys Ala Glu Pro Gly Leu Ser His Cys
            85                  90                  95

His Ala Leu Ala Thr Cys Val Asn Val Val Gly Ser Tyr Leu Cys Val
        100                 105                 110

Cys Pro Ala Gly Tyr Arg Gly Asp Gly Trp His Cys Glu Cys Ser Pro
    115                 120                 125

Gly Ser Cys Gly Pro Gly Leu Asp Cys Val Pro Glu Gly Asp Ala Leu
```

-continued

```
                130                 135                 140
Val Cys Ala Asp Pro Cys Gln Ala His Arg Thr Leu Asp Glu Tyr Trp
145                 150                 155                 160
Arg Ser Thr Glu Tyr Gly Glu Gly Tyr Ala Cys Asp Thr Asp Leu Arg
                165                 170                 175
Gly Trp Tyr Arg Phe Val Gly Gln Gly Gly Ala Arg Met Ala Glu Thr
                180                 185                 190
Cys Val Pro Val Leu Arg Cys Asn Thr Ala Ala Pro Met Trp Leu Asn
                195                 200                 205
Gly Thr His Pro Ser Ser Asp Glu Gly Ile Val Ser Arg Lys Ala Cys
        210                 215                 220
Ala His Trp Ser Gly His Cys Cys Leu Trp Asp Ala Ser Val Gln Val
225                 230                 235                 240
Lys Ala Cys Ala Gly Gly Tyr Tyr Val Tyr Asn Leu Thr Ala Pro Pro
                245                 250                 255
Glu Cys His Leu Ala Tyr Cys Thr Asp Pro Ser Ser Val Glu Gly Thr
                260                 265                 270
Cys Glu Glu Cys Ser Ile Asp Glu Asp Cys Lys Ser Asn Asn Gly Arg
        275                 280                 285
Trp His Cys Gln Cys Lys Gln Asp Phe Asn Ile Thr Asp Ile Ser Leu
        290                 295                 300
Leu Glu His Arg Leu Glu Cys Gly Ala Asn Asp Met Lys Val Ser Leu
305                 310                 315                 320
Gly Lys Cys Gln Leu Lys Ser Leu Gly Phe Asp Lys Val Phe Met Tyr
                325                 330                 335
Leu Ser Asp Ser Arg Cys Ser Gly Phe Asn Asp Arg Asp Asn Arg Asp
                340                 345                 350
Trp Val Ser Val Val Thr Pro Ala Arg Asp Gly Pro Cys Gly Thr Val
                355                 360                 365
Leu Thr Arg Asn Glu Thr His Ala Thr Tyr Ser Asn Thr Leu Tyr Leu
        370                 375                 380
Ala Asp Glu Ile Ile Ile Arg Asp Leu Asn Ile Lys Ile Asn Phe Ala
385                 390                 395                 400
Cys Ser Tyr Pro Leu Asp Met Lys Val Ser Leu Lys Thr Ala Leu Gln
                405                 410                 415
Pro Met Val Ser Ala Leu Asn Ile Arg Val Gly Gly Thr Gly Met Phe
                420                 425                 430
Thr Val Arg Met Ala Leu Phe Gln Thr Pro Ser Tyr Thr Gln Pro Tyr
                435                 440                 445
Gln Gly Ser Ser Val Thr Leu Ser Thr Glu Ala Phe Leu Tyr Val Gly
        450                 455                 460
Thr Met Leu Asp Gly Gly Asp Leu Ser Arg Phe Ala Leu Leu Met Thr
465                 470                 475                 480
Asn Cys Tyr Ala Thr Pro Ser Ser Asn Ala Thr Asp Pro Leu Lys Tyr
                485                 490                 495
Phe Ile Ile Gln Asp Arg Cys Pro His Thr Arg Asp Ser Thr Ile Gln
                500                 505                 510
Val Val Glu Asn Gly Glu Ser Ser Gln Gly Arg Phe Ser Val Gln Met
        515                 520                 525
Phe Arg Phe Ala Gly Asn Tyr Asp Leu Val Tyr Leu His Cys Glu Val
        530                 535                 540
Tyr Leu Cys Asp Thr Met Asn Glu Lys Cys Lys Pro Thr Cys Ser Gly
545                 550                 555                 560
```

Thr Arg Phe

<210> SEQ ID NO 7
<211> LENGTH: 410
<212> TYPE: PRT
<213> ORGANISM: Homo sapiens

<400> SEQUENCE: 7

Asp Thr Ser Glu Ala Arg Trp Cys Ser Glu Cys His Ser Asn Ala Thr
1               5                   10                  15

Cys Thr Glu Asp Glu Ala Val Thr Thr Cys Thr Cys Gln Glu Gly Phe
            20                  25                  30

Thr Gly Asp Gly Leu Thr Cys Val Asp Leu Asp Glu Cys Ala Ile Pro
        35                  40                  45

Gly Ala His Asn Cys Ser Ala Asn Ser Ser Cys Val Asn Thr Pro Gly
    50                  55                  60

Ser Phe Ser Cys Val Cys Pro Glu Gly Phe Arg Leu Ser Pro Gly Leu
65                  70                  75                  80

Gly Cys Thr Asp Val Asp Glu Cys Ala Glu Pro Gly Leu Ser His Cys
                85                  90                  95

His Ala Leu Ala Thr Cys Val Asn Val Val Gly Ser Tyr Leu Cys Val
                100                 105                 110

Cys Pro Ala Gly Tyr Arg Gly Asp Gly Trp His Cys Glu Cys Ser Pro
            115                 120                 125

Gly Ser Cys Gly Pro Gly Leu Asp Cys Val Pro Glu Gly Asp Ala Leu
        130                 135                 140

Val Cys Ala Asp Pro Cys Gln Ala His Arg Thr Leu Asp Glu Tyr Trp
145                 150                 155                 160

Arg Ser Thr Glu Tyr Gly Glu Gly Tyr Ala Cys Asp Thr Asp Leu Arg
                165                 170                 175

Gly Trp Tyr Arg Phe Val Gly Gln Gly Gly Ala Arg Met Ala Glu Thr
            180                 185                 190

Cys Val Pro Val Leu Arg Cys Asn Thr Ala Ala Pro Met Trp Leu Asn
        195                 200                 205

Gly Thr His Pro Ser Ser Asp Glu Gly Ile Val Ser Arg Lys Ala Cys
    210                 215                 220

Ala His Trp Ser Gly His Cys Cys Leu Trp Asp Ala Ser Val Gln Val
225                 230                 235                 240

Lys Ala Cys Ala Gly Gly Tyr Tyr Val Tyr Asn Leu Thr Ala Pro Pro
                245                 250                 255

Glu Cys His Leu Ala Tyr Cys Thr Asp Pro Ser Ser Val Glu Gly Thr
            260                 265                 270

Cys Glu Glu Cys Ser Ile Asp Glu Asp Cys Lys Ser Asn Asn Gly Arg
        275                 280                 285

Trp His Cys Gln Cys Lys Gln Asp Phe Asn Ile Thr Asp Ile Ser Leu
    290                 295                 300

Leu Glu His Arg Leu Glu Cys Gly Ala Asn Asp Met Lys Val Ser Leu
305                 310                 315                 320

Gly Lys Cys Gln Leu Lys Ser Leu Gly Phe Asp Lys Val Phe Met Tyr
                325                 330                 335

Leu Ser Asp Ser Arg Cys Ser Gly Phe Asn Asp Arg Asp Asn Arg Asp
            340                 345                 350

Trp Val Ser Val Val Thr Pro Ala Arg Asp Gly Pro Cys Gly Thr Val
        355                 360                 365

```
Leu Thr Arg Asn Glu Thr His Ala Thr Tyr Ser Asn Thr Leu Tyr Leu
    370                 375                 380

Ala Asp Glu Ile Ile Ile Arg Asp Leu Asn Ile Lys Ile Asn Phe Ala
385                 390                 395                 400

Cys Ser Tyr Pro Leu Asp Met Lys Val Ser
                405             410
```